US008747282B2

(12) United States Patent
Lannon et al.

(10) Patent No.: US 8,747,282 B2
(45) Date of Patent: Jun. 10, 2014

(54) PROCESS AND APPARATUS FOR EXERCISING AN OPERATOR

(75) Inventors: Michael G. Lannon, Orleans, MA (US); Mary Obana, Orleans, MA (US); Carl R. Spoeth, Jr., Bayonet Point, FL (US); Ian N. Whitehead, Concord, MA (US); Jeffrey A. Pearson, Plymouth, MA (US); Jonathan S. Hazelwood, Watertown, MA (US); Joshua J. Roman, Jamaica Plain, MA (US); David L. Peterman, Marshfield, MA (US)

(73) Assignee: Michael G. Lannon, Orleans, MA (US)

( * ) Notice: Subject to any disclaimer, the term of this patent is extended or adjusted under 35 U.S.C. 154(b) by 0 days.

(21) Appl. No.: 13/362,074

(22) Filed: Jan. 31, 2012

(65) Prior Publication Data

US 2012/0302405 A1 Nov. 29, 2012

Related U.S. Application Data

(60) Continuation of application No. 12/823,287, filed on Jun. 25, 2010, now Pat. No. 8,105,209, which is a division of application No. 11/818,624, filed on Jun. 15, 2007, now Pat. No. 7,794,359, which is a continuation-in-part of application No. 11/125,569, filed on May 10, 2005, now Pat. No. 8,105,207.

(60) Provisional application No. 60/662,935, filed on Mar. 16, 2005, provisional application No. 60/569,535, filed on May 10, 2004.

(51) Int. Cl.
*A63B 24/00* (2006.01)

(52) U.S. Cl.
USPC .................. 482/8; 482/1; 482/9; 482/901

(58) Field of Classification Search
USPC .......................................... 482/1–9, 900–902
See application file for complete search history.

(56) References Cited

U.S. PATENT DOCUMENTS

| | | | |
|---|---|---|---|
| 3,735,101 A | 5/1973 | Stewart | |
| 3,869,121 A | 3/1975 | Flavell | |
| 4,158,511 A | 6/1979 | Herbenar | |
| 4,493,485 A | 1/1985 | Jones | |
| 4,549,555 A | 10/1985 | Fraser et al. | |

(Continued)

FOREIGN PATENT DOCUMENTS

WO  WO2010/019644  2/2010

OTHER PUBLICATIONS

PCT International Search Report and Written Opinion, PCT/US2009/053518, dated Feb. 22, 2010, 13 pages.

*Primary Examiner* — Glenn Richman
(74) *Attorney, Agent, or Firm* — Fish & Richardson P.C.

(57) ABSTRACT

A process is disclosed for enabling an operator to exercise on an exercise device. The process includes measuring a range of movement of the operator during exercising on the exercise device for generating an electronic range of movement data. A strength is measured of the operator during exercising on the exercise device for generating an electronic strength data. An electronic program is designed based on the electronic range of movement data and the electronic strength data. The electronic program is stored in an electronic media. The electronic program is displayed as a moving scale on a screen for instructing the operator to exercise at the same rate as the moving scale to complete the exercise in a timely and controlled matter.

24 Claims, 27 Drawing Sheets

(56) References Cited

U.S. PATENT DOCUMENTS

| | | | |
|---|---|---|---|
| 4,728,099 A | 3/1988 | Pitre | |
| 4,735,195 A | 4/1988 | Blum et al. | |
| 4,746,113 A | 5/1988 | Kissel | |
| 4,765,613 A | 8/1988 | Voris | |
| 4,817,940 A | 4/1989 | Shaw et al. | |
| 4,828,257 A * | 5/1989 | Dyer et al. | 482/5 |
| 4,831,242 A | 5/1989 | Englehardt et al. | |
| 4,902,009 A | 2/1990 | Jones | |
| 4,907,795 A | 3/1990 | Shaw et al. | |
| 4,911,427 A | 3/1990 | Matsumoto et al. | |
| 4,919,418 A | 4/1990 | Miller | |
| 5,018,726 A | 5/1991 | Yorioka | |
| 5,020,794 A | 6/1991 | Englehardt et al. | |
| 5,020,795 A | 6/1991 | Airy et al. | |
| 5,037,089 A | 8/1991 | Spagnuolo et al. | |
| 5,082,001 A | 1/1992 | Vannier et al. | |
| 5,149,084 A | 9/1992 | Dalebout et al. | |
| 5,216,817 A | 6/1993 | Misevich et al. | |
| 5,290,214 A | 3/1994 | Chen | |
| 5,323,784 A | 6/1994 | Shu | |
| 5,324,247 A | 6/1994 | Lepley | |
| 5,328,429 A | 7/1994 | Potash et al. | |
| 5,410,472 A | 4/1995 | Anderson | |
| 5,429,140 A | 7/1995 | Burdea et al. | |
| 5,435,799 A | 7/1995 | Lundin | |
| 5,458,548 A | 10/1995 | Crossing et al. | |
| 5,603,330 A | 2/1997 | Suga | |
| 5,653,669 A | 8/1997 | Cheng | |
| 5,655,997 A | 8/1997 | Greenberg et al. | |
| 5,679,102 A | 10/1997 | Hammer | |
| 5,704,875 A | 1/1998 | Tanabe | |
| 5,715,160 A | 2/1998 | Plotke | |
| 5,740,813 A | 4/1998 | Ogata et al. | |
| 5,785,632 A | 7/1998 | Greenberg et al. | |
| 5,800,310 A | 9/1998 | Jones | |
| 5,803,870 A | 9/1998 | Buhler | |
| 5,810,747 A | 9/1998 | Brudny et al. | |
| 5,853,351 A | 12/1998 | Maruo et al. | |
| 5,879,270 A | 3/1999 | Huish et al. | |
| 5,916,063 A | 6/1999 | Alessandri | |
| 5,921,891 A | 7/1999 | Browne | |
| 5,931,763 A | 8/1999 | Alessandri | |
| 5,947,869 A | 9/1999 | Shea | |
| 5,980,429 A | 11/1999 | Nashner | |
| 6,013,009 A | 1/2000 | Karkanen | |
| 6,033,227 A | 3/2000 | Ishig | |
| 6,050,924 A | 4/2000 | Shea | |
| 6,053,844 A | 4/2000 | Clem | |
| 6,077,193 A | 6/2000 | Buhler et al. | |
| 6,117,049 A | 9/2000 | Lowe | |
| 6,190,287 B1 | 2/2001 | Nashner | |
| 6,210,301 B1 | 4/2001 | Abraham-Fuchs et al. | |
| 6,228,000 B1 | 5/2001 | Jones | |
| 6,231,481 B1 | 5/2001 | Brock | |
| 6,354,996 B1 | 3/2002 | Drinan et al. | |
| 6,358,188 B1 | 3/2002 | Ben-Yehuda et al. | |
| 6,439,893 B1 | 8/2002 | Byrd et al. | |
| 6,471,363 B1 | 10/2002 | Howell et al. | |
| 6,494,811 B1 | 12/2002 | Alessandri | |
| 6,497,638 B1 | 12/2002 | Shea | |
| 6,503,173 B2 | 1/2003 | Clem | |
| 6,527,674 B1 | 3/2003 | Clem | |
| 6,551,214 B1 | 4/2003 | Taimela | |
| 6,605,044 B2 | 8/2003 | Bimbaum | |
| 6,607,483 B1 | 8/2003 | Holland | |
| 6,626,799 B2 | 9/2003 | Watterson et al. | |
| 6,626,800 B1 | 9/2003 | Casier | |
| 6,626,805 B1 | 9/2003 | Lightbody | |
| 6,632,158 B1 | 10/2003 | Nashner | |
| 6,632,161 B1 | 10/2003 | Nir | |
| 6,648,798 B2 | 11/2003 | Yoo | |
| 6,659,946 B1 | 12/2003 | Batchelor et al. | |
| 6,669,600 B2 | 12/2003 | Warner | |
| 6,672,991 B2 | 1/2004 | O'Malley | |
| 6,687,535 B2 | 2/2004 | Hautala et al. | |
| 6,689,057 B1 | 2/2004 | Shinsel et al. | |
| 6,719,667 B2 | 4/2004 | Wong et al. | |
| 6,740,007 B2 * | 5/2004 | Gordon et al. | 482/9 |
| 6,746,370 B1 | 6/2004 | Fleming et al. | |
| 6,793,607 B2 | 9/2004 | Neil | |
| 6,808,472 B1 | 10/2004 | Hickman | |
| 6,863,641 B1 | 3/2005 | Brown et al. | |
| 6,866,613 B1 | 3/2005 | Brown et al. | |
| 6,899,442 B2 | 5/2005 | Howell et al. | |
| 6,913,559 B2 | 7/2005 | Smith | |
| 6,916,274 B2 | 7/2005 | Glusco | |
| 6,918,858 B2 | 7/2005 | Watterson et al. | |
| 6,921,351 B1 | 7/2005 | Hickman et al. | |
| 6,973,688 B2 | 12/2005 | Barker et al. | |
| 7,163,488 B2 | 1/2007 | Anders et al. | |
| 7,243,892 B2 | 7/2007 | Pfister | |
| 7,369,672 B2 | 5/2008 | Hirschhorn | |
| 7,410,138 B2 | 8/2008 | Parsons | |
| 8,103,517 B2 | 1/2012 | Hinnebusch | |
| 2004/0171464 A1 | 9/2004 | Ashby et al. | |
| 2005/0041048 A1 | 2/2005 | Hillman et al. | |
| 2005/0239600 A1 | 10/2005 | Liang et al. | |
| 2007/0265138 A1 | 11/2007 | Ashby | |

\* cited by examiner

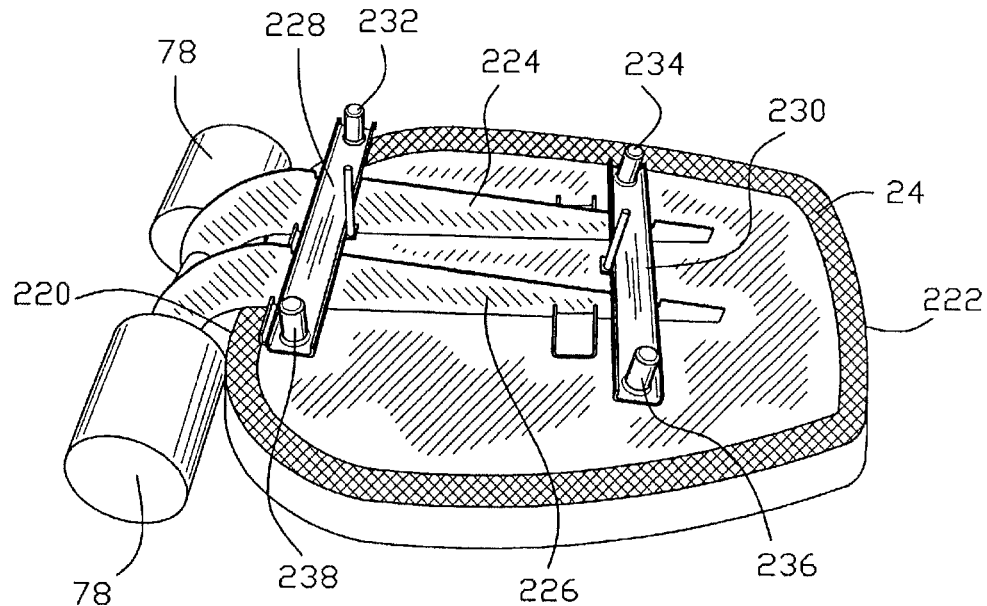
FIG. 17
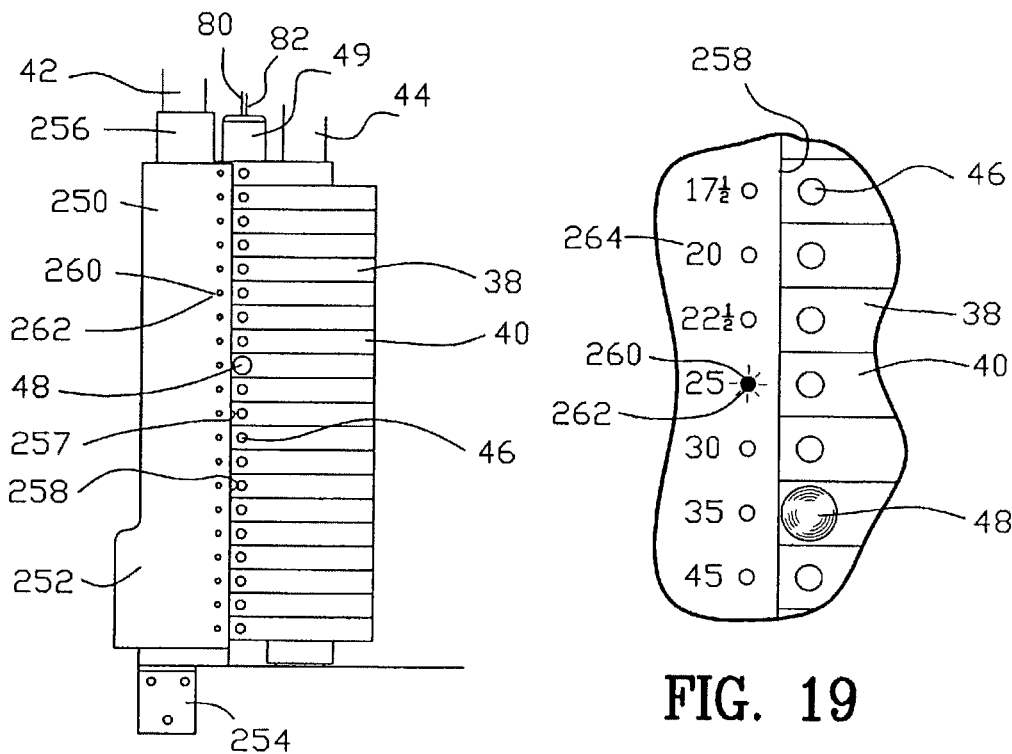
FIG. 18
FIG. 19

PROCESS AND APPARATUS FOR EXERCISING AN OPERATOR

CROSS-REFERENCE TO RELATED APPLICATIONS

This application is a continuation (and claims the benefit of priority under 35 USC 120) of U.S. application Ser. No. 12/823,287, filed Jun. 25, 2010, now U.S. Pat. No. 8,105,209 which is a divisional (and claims the benefit of priority under 35 U.S.C. §121) of U.S. application Ser. No . 11/818,624, filed Jun. 15, 2007, now U.S. Pat. No. 7,794,359 which is a continuation-in-part of U.S. application Ser. No. 11/125,569, filed May 10, 2005 now U.S. Pat. No. 8,105,207, which claims the benefit of priority from both U.S. provisional application Ser. No. 60/662,935 filed Mar. 16, 2005, and U.S. provisional application Ser. No. 60/569,535, filed May 10, 2004. The disclosures of these prior applications are considered part of (and are incorporated by reference in) the disclosure of this application.

BACKGROUND OF THE INVENTION

1. Field of the Invention

This invention relates to exercising and more particularly to the improved apparatus for enabling an operator to exercise.

2. Background of the Invention

Regular exercise and physical activity are extremely important and beneficial for long-term health and well-being. Some of the benefits of exercise and physical activity include a reduced risk of premature death, heart disease, high blood pressure, cholesterol and a reduced risk of developing colon cancer and diabetes. In addition, the benefits of exercise and physical activity further include a reduced body weight, a reduced risk of depression and improved psychological well-being.

As such, various types of exercising equipment have been proposed by the prior art for enabling an operator to exercise. Currently used exercising equipment is difficult to use and requires the expertise of an instructor or a personal trainer to teach the user the proper techniques and usage of the equipment. The user must also remember the required settings for the equipment and understand when these settings should be changed as the physical ability and strength of the user increases. Unfortunately, because of these limitations in order for an individual to properly and effectively utilize the exercise equipment the supervision of an experienced trainer is required.

The need exists for an exercise device which minimizes the need for extensive instruction from a personal trainer or instructor. Further, a device capable of recording the progress of the user would enable the user to more easily match the settings of the device to the improvement in the physical condition of the user. The ability of the device to record strength, and personal physical condition of the user such as heart rate would further increase the value of the device to the user. By combining these features in a device which is simple to maintain would provide a significant contribution to the art. The following U.S. patents are the examples of an attempt of the prior art to solve these problems.

U.S. Pat. No. 5,785,632 to Greenberg, et al. discloses an apparatus for providing feedback to a user of a weight stack machine having weights for lifting and an enclosure adapted for attachment to the weight stack machine. A weight sensor for determining the number of weights lifted is provided as well as an means for detecting the motion of the weights during a lift. An electronic detector is operatively coupled to the weight sensor and the encoder for computing data describing the number of weights lifted. An interface for transmitting the computed data from the electronic detector to a central storage and the display is provided. The interface also receives information from the central storage and displays it on the display.

U.S. Pat. No. 5,931,763 to Alessandri discloses a system for programming training on exercise apparatus, with a series of exercises defining a personalized program, includes a central unit with first processor and a bi-directional data transferor; a portable medium, with a portable memory for data storage; a plurality of stations, not connected to one another by a data transmission line, and located at the exercise apparatus, with a second processor and a bi-directional data transferor from and to the portable medium, so as to receive as input the data in the portable memory relative to the exercise to be performed on an individual apparatus, for programming the apparatus, and so as to transfer as output to the portable memory upon completion of the exercise, data relative to the performance of the exercise so as to allow such data to be controlled. The first processor, after receiving from the portable medium the actual data for an exercise just completed, through the bi-directional data transferor of the said central unit, being capable of modifying the program in accordance with the actual data received. The central unit has data storage and/or comparator means, connected to the first processor, or the plurality of stations have data storage and/or comparator means, connected to the second processor, in order to allow the use of specific data.

U.S. Pat. No. 6,228,000 to Jones discloses a method and apparatus for testing the muscle strength of a subject wherein both static and dynamic strength tests are conducted on the subject during which forces exerted by the muscles are measured by devices which are connected to a computer and a display screen for displaying the strength of the muscles at different positions of a subject's body part. In the dynamic strength test, the subject moves a movement arm by exerting the muscles to be tested. The movement arm is connected to a resistance weight to oppose movement by the subject. In the static strength test, the movement arm is fixed in position and the subject exerts a body part against the movement arm upon exertion of the muscles to be tested. Force and angle measuring devices are connected to the movement arm and the computer for enabling the muscle strength to be displayed in terms of torque at various angular positions of the body part.

Although the aforementioned prior art have contributed to the development of the art of exercising equipment, none of these prior art patents have solved the needs of this art.

Therefore, it is an object of the present invention to provide an improved apparatus for enabling an operator to exercise.

Another object of this invention is to provide an improved apparatus for placing an object between a storage position to a usage position.

Another object of this invention is to provide an improved pivotable holder wherein the pivotable holder's structure, attachment mechanism and locking device are simplified.

Another object of this invention is to provide an improved pivotable holder wherein the pivotable holder's attachment to a support base does not require drastically altering the support base.

Another object of this invention is to provide an improved exercise device requiring a minimum of expert instruction.

Another object of this invention is to provide an improved exercise device capable of recording the progress and physical characteristics of the user in a portable format.

Another object of this invention is to provide an improved exercise device which is simple to maintain.

Another object of this invention is to provide an improved process of enabling the operator to exercise on a exercise device.

Another object of this invention is to provide an improved process generating a performance data based upon the effectiveness of the operator on a exercise device.

Another object of this invention is to provide an improved electrical network for transferring data between an exercise device and a storage device.

Another object of this invention is to provide an improved electrical network for transferring data between an exercise device and a processor.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention and the detailed description describing the preferred embodiment of the invention.

SUMMARY OF THE INVENTION

A specific embodiment of the present invention is shown in the attached drawings. For the purpose of summarizing the invention, the invention relates to a process of enabling an operator to exercise on an exercise device. The process comprises the steps of measuring a range of movement of the operator during exercising on the exercise device for generating an electronic range of movement data. The strength of the operator is measured during exercising on the exercise device for generating an electronic strength data. An electronic program is designed based on the electronic range of movement data and the electronic strength data. The electronic program is stored in an electronic media. The electronic program is displayed as a moving scale on a screen for instructing the operator to exercise at the same rate as the moving scale to complete the exercise in a timely and controlled matter.

In a more specific embodiment of the invention, the process comprises the steps of generating a performance data based upon the effectiveness of the operator in maintaining the same exercise rate or pacing as the moving scale on the screen. A performance data is generated based upon the effectiveness of the operator in maintaining the same exercise rate or pacing as the moving scale on the screen. The performance data is stored in a portable electronic storage device through an electronic wire link. In another embodiment of the invention, the performance data based is stored in a network electronic storage device through an electronic wireless link.

The invention further relates to a plurality of exercise machines for enabling the operator to exercise. Each of the plurality of exercise machines have an exercise electric storage for storing data relative to the exercise of the operator on the plurality of exercise machines respectively. A remote computer has a remote electric storage for storing the data relative to the exercise of the operator on the plurality of exercise machines respectively. A network transmits and receives the data from the remote computer. A link electrically couples the plurality of exercise machines to the network for transmitting and receiving the data between the plurality of exercise machines and the remote computer.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 17 is a bottom view of the seat;

FIG. 18 is a magnified view of a lower portion of FIG. 5;

FIG. 19 is a magnified view of a portion of FIG. 18;

Similar reference characters refer to similar parts throughout the several Figures of the drawings.

DETAILED DISCUSSION

Figure 1:
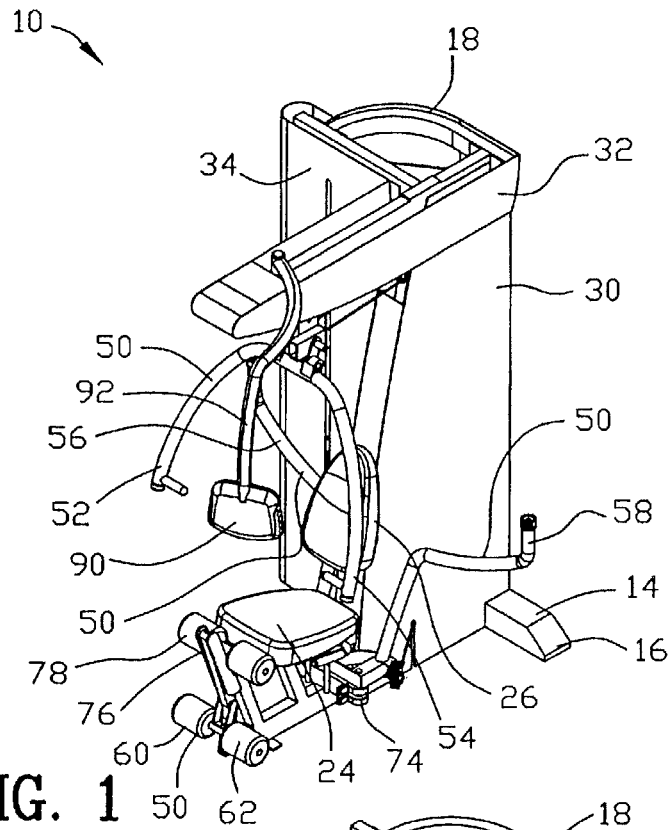
FIG. 1 is an isometric view of an apparatus for enabling an operator to exercise incorporating the present invention.
Figure 2:
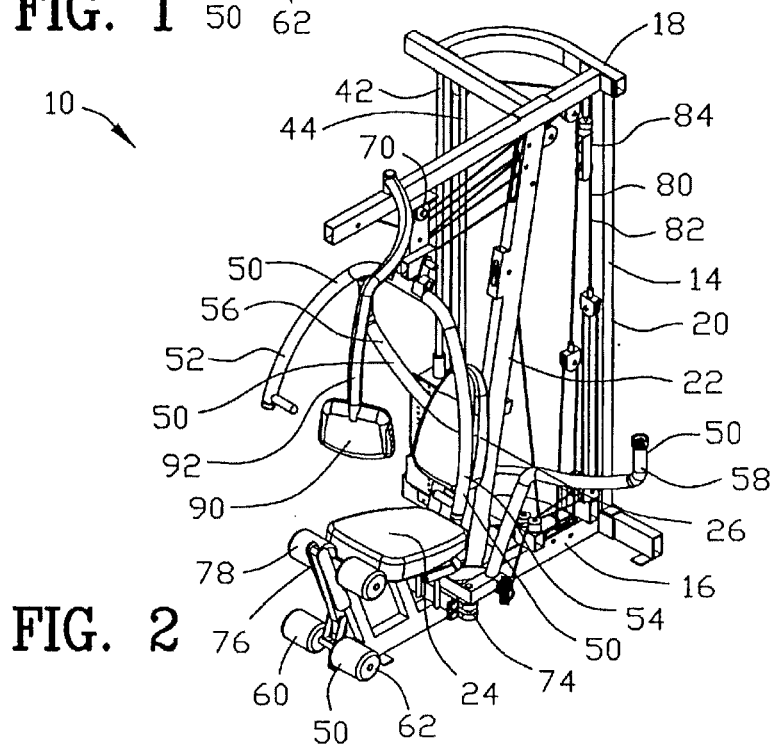
FIG. 2 is an isometric view of the apparatus of FIG. 1 without a plurality of shrouds.
Figure 3:
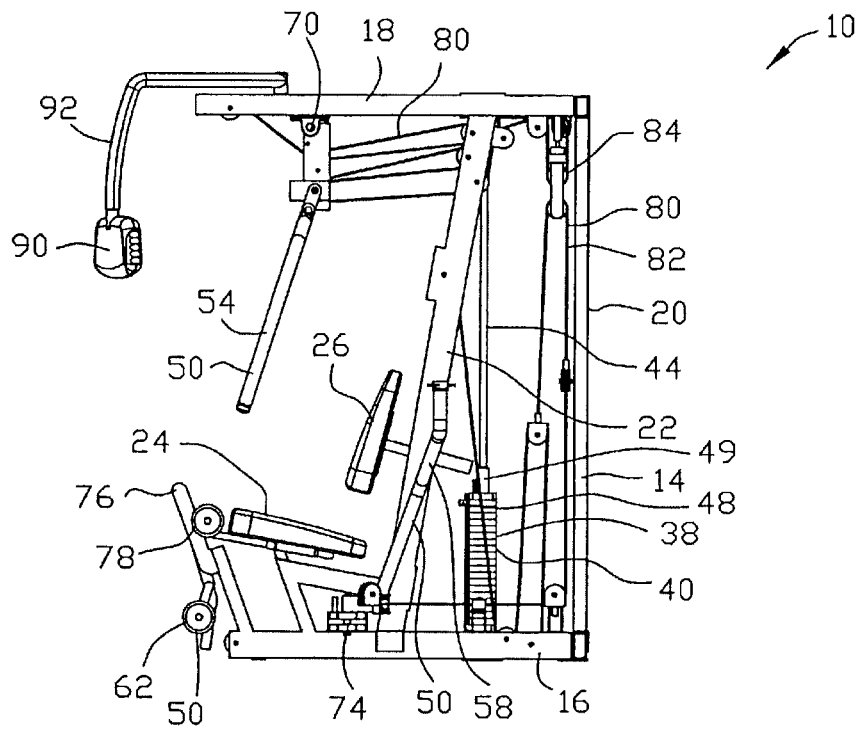
FIG. 3 is a right side view of FIG. 2.
Figure 4:
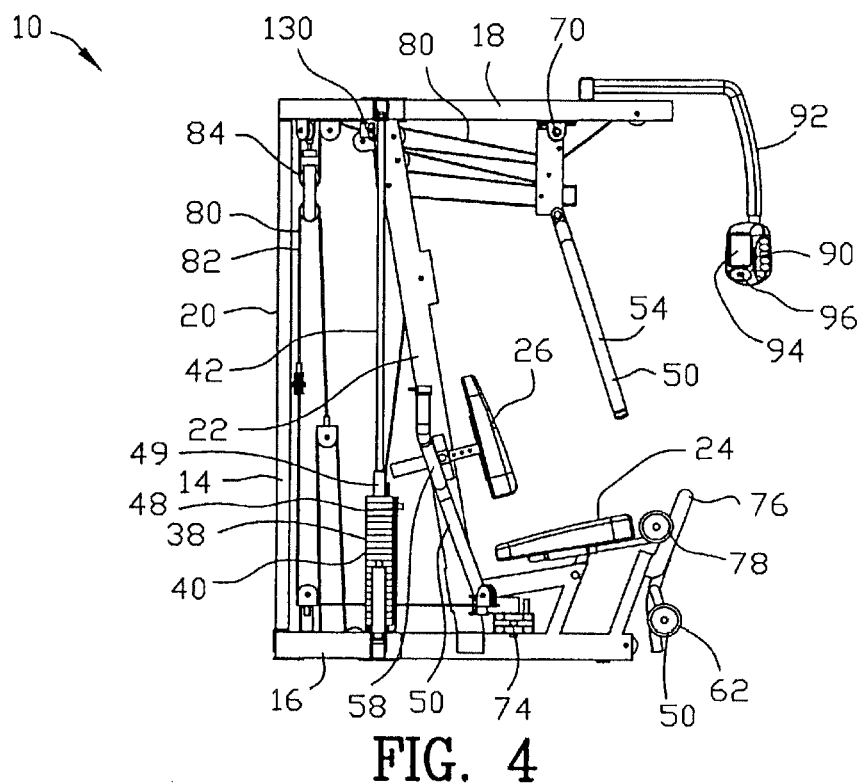
FIG. 4 is a left side view of FIG. 2.
Figure 5:
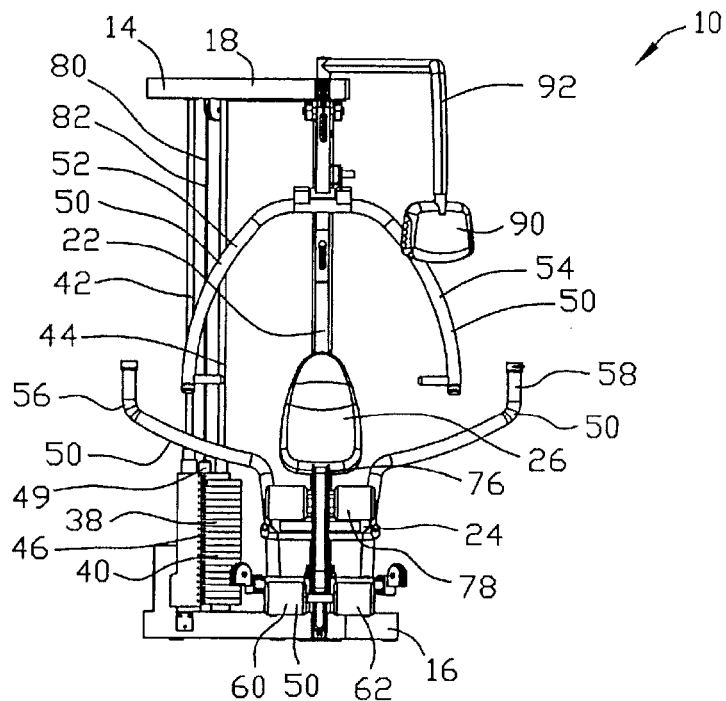
FIG. 5 is a front view of FIG. 2.
Figure 6:
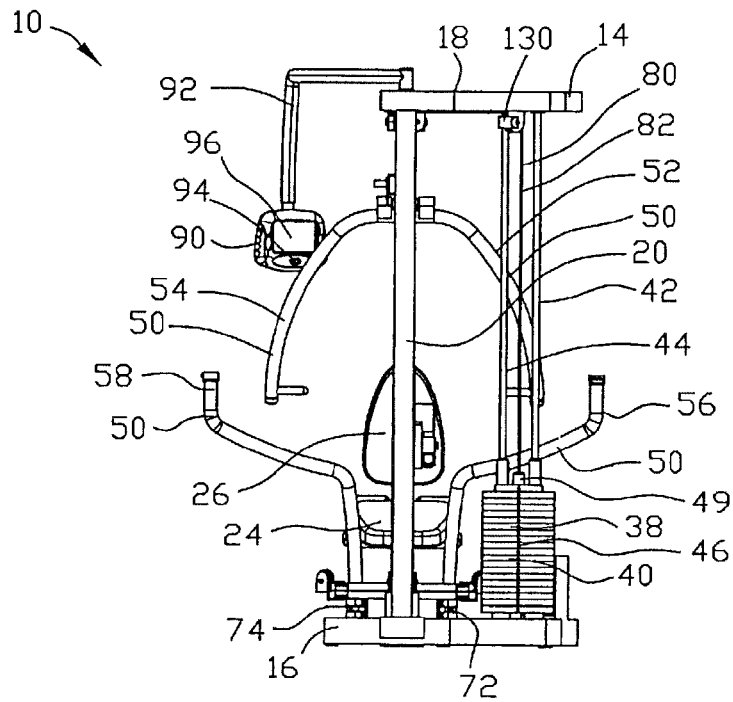
FIG. 6 is a rear view of FIG. 2.
Figure 7:
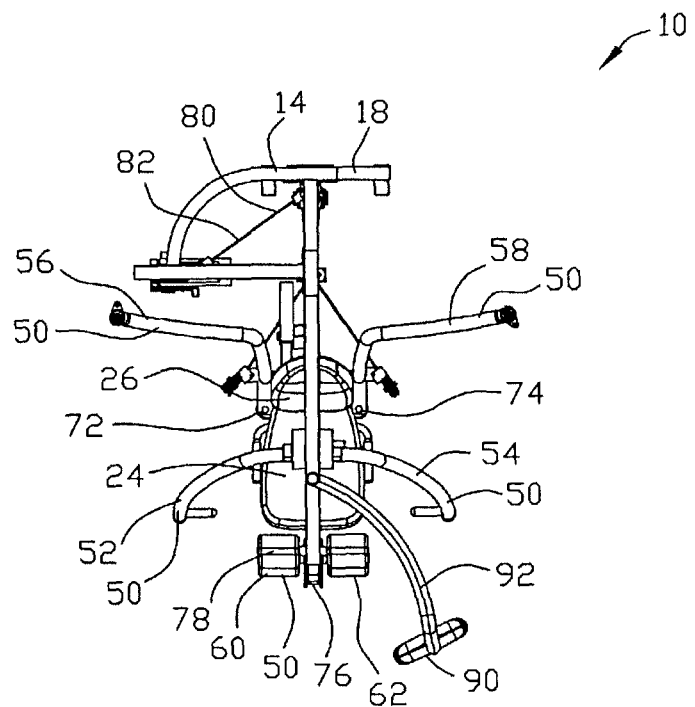
FIG. 7 is a top view of FIG. 2.
Figure 8:
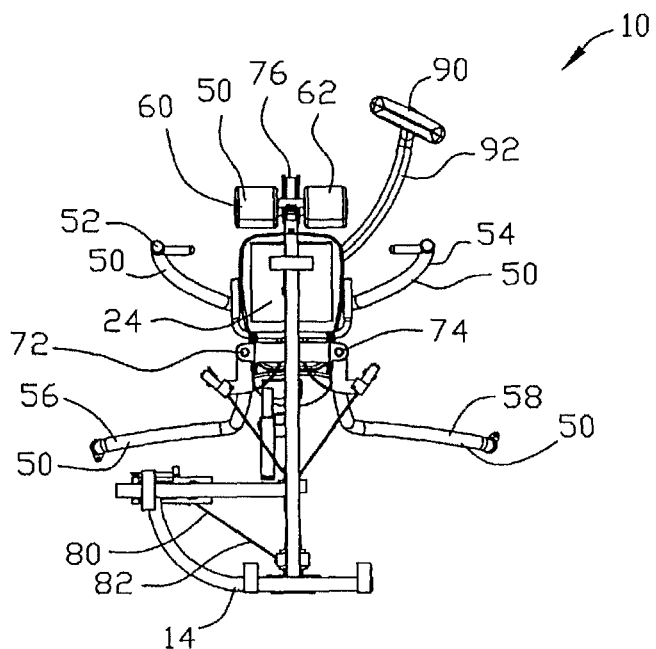
FIG. 8 is a bottom view of FIG. 2.

FIGS. 1-8 are various views of an apparatus 10 for enabling an operator 12 (not shown) to exercise incorporating the present invention. The frame 14 includes a lower frame unit 16 and an upper frame unit 18 separated and supported by a first frame coupling 20 and a second frame coupling 22. The frame 14 may be constructed from square tubing apprising steel or other similar material. The lower frame unit 16 includes a seat 24 for supporting a lower portion of the operator 12. The second frame coupling 22 includes a back rest 26 for supporting an upper portion of the operator 12.

The apparatus 10 may further include a central frame shroud 30 for concealing the first and second frame coupling 20 and 22. The upper frame unit 18 may include an upper frame shroud 32 for concealing the upper frame unit 18. The central frame shroud 30 and the upper frame shroud 32 may be constructed of a polymeric material or other similar material.

A load 38 is positioned on the frame 14 by providing a first and a second weight guide 42 and 44 extending from the lower frame unit 16 to the upper frame unit 18. The load 38 provides a resistive force to resists a force exerted by the operator 12. The load 38 may further comprise a plurality of weights 40 each including a horizontal weight cavity 46 for receiving a pin 48. Each of the plurality of weights 40 also include a vertical bore 47 (not shown) for receiving a lifter pin 49. The lifter pin 49 has a plurality of horizontal pin cavities 45 (not shown) for receiving the pin 48. To lift the load 38 the pin 48 is inserted into a horizontal weight cavity 46 of one of the plurality of weights 40 and engages one of the horizontal pin cavities 45. A vertical force is then applied to the lifter pin 49 to lift the load 38. The plurality of weights 40 may be constructed of plate steel or other similar material. The load 38 may be concealed by a weight frame shroud 34 secured to the frame 14. The weight frame shroud 34 may be constructed of a polymeric material or other similar material.

The apparatus 10 further includes a press 50 positioned on the frame 14 for displacement by the operator 12. The press 50 may include a first and second chest press 52 and 54 for exercising the chest muscles of the operator 12. The first and second chest press 52 and 54 are secured to the frame 14 by a chest pivot 70 secured to the upper frame unit 18. The press 50 may also include a first and second back press 56 and 58 for exercising the back muscles of the operator 12. The first and second back press 56 and 58 are secured to the frame 14 by a first and second back pivot 72 and 74 respectively. The first and second back pivot 72 and 74 are secured to the lower frame unit 16. The press 50 may also include a first and second leg press 60 and 62 for exercising the leg muscles of the operator 12. The first and second leg press 60 and 62 are secured to the frame 14 by a leg press pivot 76 secured to the lower frame unit 16. The frame 14 includes a leg rest 78 for cushioning the leg of the operator 12. The apparatus as shown with a chest press, a back press and leg press, however it should be understood that other presses may be utilized with the apparatus 10. The press 50 is joined to the load 38 by a linkage 80 such that the load is displaced upon displacement of the press 50 by the operator 12. The linkage 80 may include a plurality of cables 82 comprising steel or other similar material extending from the lifter pin 49 to the press 50. The linkage 80 may be routed from the load 38 to the press by a plurality of pulleys 84.

The plurality of cables 82, plurality of pulleys 84 and plurality of weights 40 are concealed by the central frame shroud 30, the upper frame shroud 32 and the weight frame shroud 34. The central frame shroud 30, upper frame shroud 32 and weight frame shroud 34 serve to prohibit access to the plurality of cables 82, plurality of pulleys 84 and plurality of weights 40 in order to prevent injury to the operator 12 or others. The central frame shroud 30, the upper frame shroud 32 and the weight frame shroud 34 also serve to make the apparatus 10 aesthetically pleasing.

Figure 9:
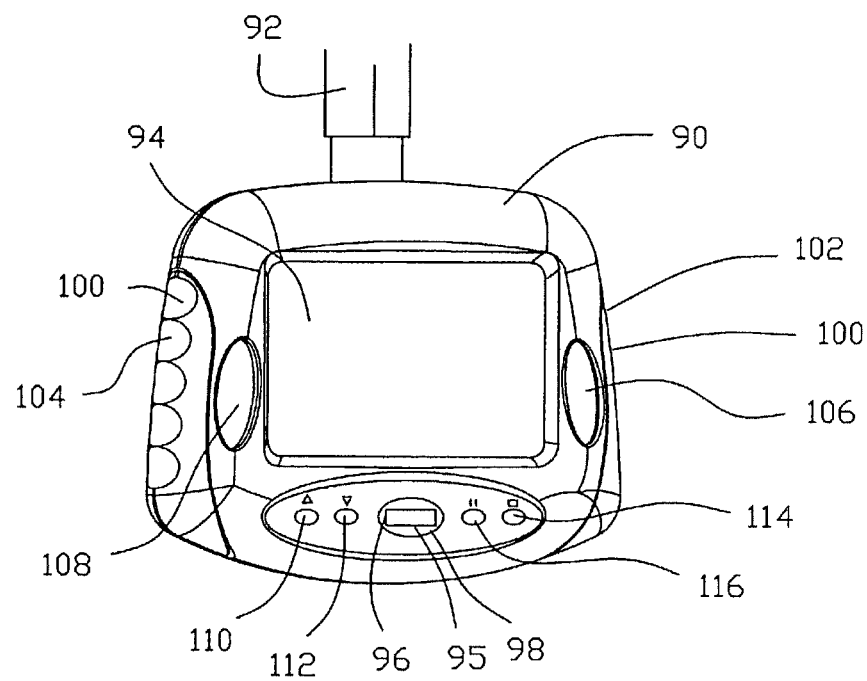
FIG. 9 is a magnified front view of a display.
Figure 10:
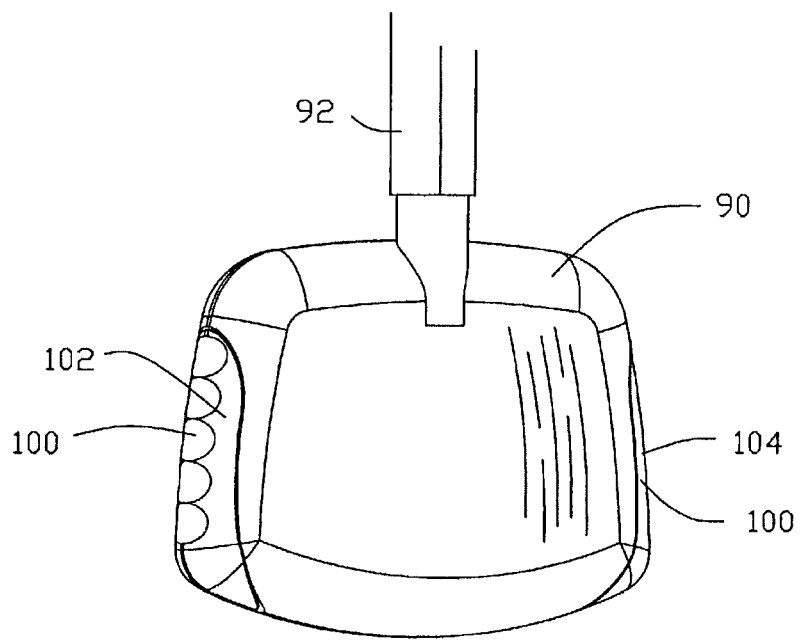
FIG. 10 is a rear view of FIG. 9.

FIGS. 9 and 10 are enlarged views of portions of FIGS. 1-8 illustrating a user interface module (UI) 90. The apparatus 10 includes a user interface module 90 secured to the upper frame unit 18 of the frame 14 by a support arm 92. The user interface module 90 includes a liquid crystal touch screen display 94 for presenting visual data and inputting data. The user interface module 90 includes an input port 95 for receiving a memory storage 96 for storing data. The input port 95 may include a USB port or other data port. The memory storage 96 may include a removable memory device 98 or other portable memory storage. The user interface module 90 also includes a contact 100 for measuring a heart rate and a body fat of the operator 12. The contact 100 may include a first and a second pad 102 and 104 positioned on either side of the user interface module 90. The contact 100 measures the heart rate of the operator 12 by positioning his hands upon the first and second pads 102 and 104. The first and second pads 102 and 104 determine the heart rate of the operator 12 by the contact method. The contact 100 can also measure the body fat of the operator by positioning his hands upon the first and second pads 102 and 104. The first and second pad 102 and 104 determine the body fat of the operator 12 by a Body Fat PCB technology or the bio-impedance method.

The user interface module 90 may further include a first and second speaker 106 and 108 creating audible signals to provide instructions or confirmation of an input into the user interface module 90. The user interface module 90 also includes a first and second function button 110 and 112 for increasing or decreasing a function. In addition, the user interface module 90 may include a stop button 114 and a pause button 116 for either terminating the exercising instruction or pausing the exercising instruction.

Figures 11, 12:
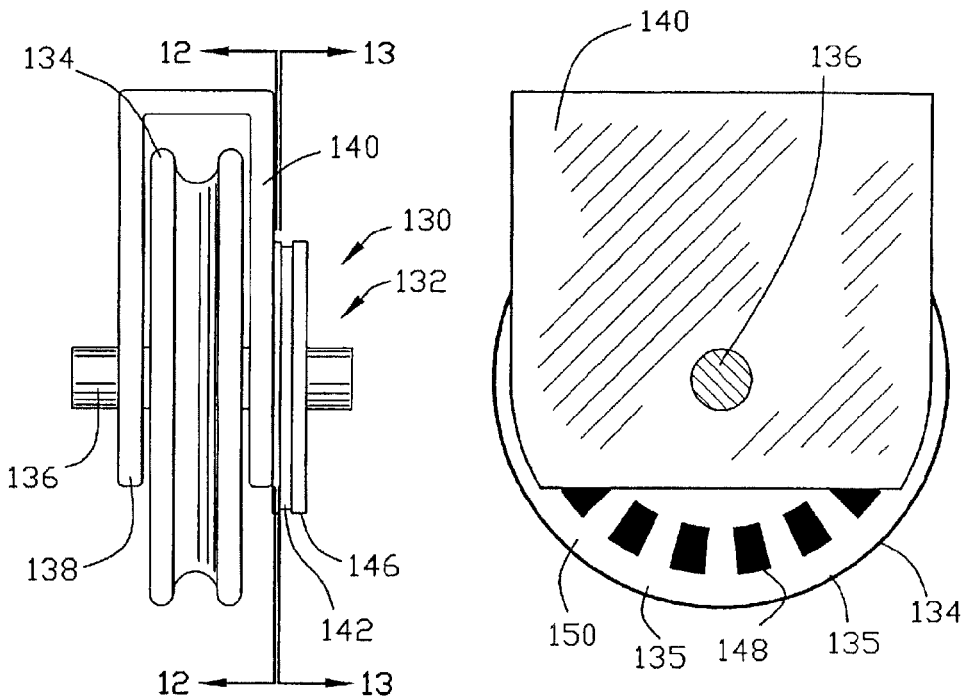
FIG. 11 is a front view of a pulley and a sensor for measuring a displacement and speed of a linkage.
FIG. 12 is a sectional view along line 12-12 in FIG. 11.
Figures 13, 14:
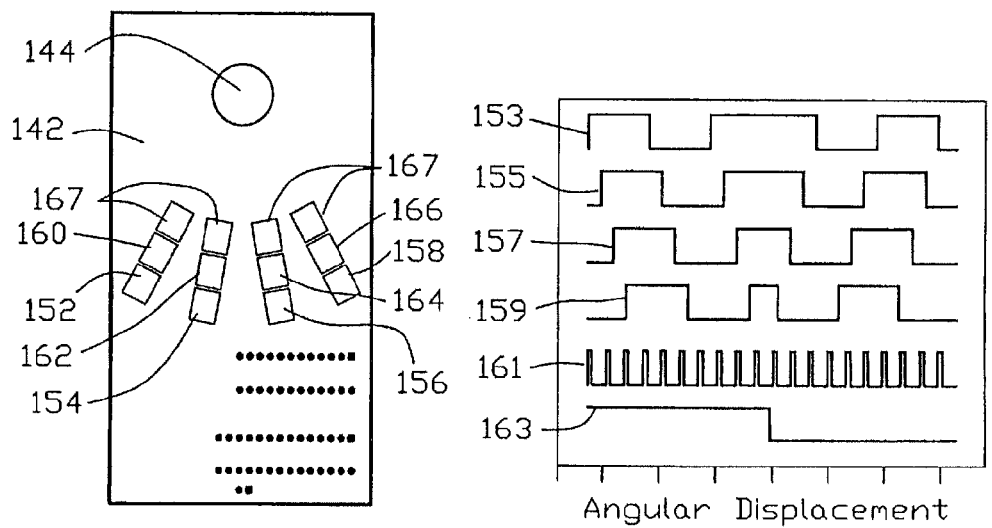
FIG. 13 is a sectional view along line 13-13 in FIG. 11.
FIG. 14 is chart illustrating the plurality of electrical pulse signals from a sensor, a count per turn of a sensor pulley and the rotational direction of the sensor pulley.

FIGS. 11-13 are various views of a sensor 130 for measuring a displacement and a speed of the linkage 80. The sensor 130 is positioned on the upper frame unit 18 of the frame 14. The sensor 130 may include a rotary optical encoder 132. The rotary optical encoder 132 comprises a sensor pulley 134 rotating about a shaft 136. The sensor pulley 134 is retained on the shaft 136 by a first pulley retainer 138 and a second pulley retainer 140. A sensor board 142 is positioned adjacent to the sensor pulley 134. The sensor board 142 includes a shaft aperture 144 for engaging the shaft 136. The sensor board 142 is retained adjacent to the sensor pulley 134 by a sensor retainer 146. The sensor pulley 134 has an absorbent surface 148 adjacent to a reflective surface 150. The sensor board 142 has a first, second, third and fourth reflective optical sensors 152, 154, 156 and 158 respectively. In addition, the sensor board 142 has a first, second, third and fourth infrared LEDs 160, 162, 164 and 166 respectively. The reflective optical sensors 152, 154, 156 and 158 and infrared LEDs 160, 162, 164 and 166 are utilized at phase angles of 0, 45, 90 and 135 degrees. As the sensor pulley 134 is rotated about the shaft 136, the light emitted from the first, second, third and fourth infrared LEDs 160, 162, 164 and 166 are either reflected by the reflected surface 150 or absorbed by the absorbent surface 148 of the sensor pulley 134. Light emitted from the first, second, third and fourth infrared LEDs 160, 162, 164 and 166 that are reflected off the reflected surface 150 will strike the reflective optical sensors 152, 154, 156 and 158 respectively. Upon the reflective optical sensors 152, 154, 156 and 158 receiving a light emission, the reflective optical sensors 152, 154, 156 and 158 are switched on to allow current flow. When the reflective optical sensors 152, 154, 156 and 158 are not receiving a light emission, the reflective optical sensors 152, 154, 156 and 158 are switched off to terminate current flow. The result of the reflective optical sensors 152, 154, 156 and 158 switching on and off produce a pulse electrical signal.

FIG. 14 illustrates a first, second, third and fourth electrical signal 153, 155, 157 and 159 produced by the reflective optical sensors 152, 154, 156 and 158 respectively. After the pulse electrical signals are amplified and converted, both the angular displacement and the rotational direction of the sensor pulley 134 can be determined. The angular displacement of the sensor pulley 134 is converted to a count 161 per turn of the sensor pulley 134. The rotational direction of the sensor pulley 134 is converted to a direction 163 of the sensor pulley 134.

Each of the reflective optical sensors 152, 154, 156 and 158 and infrared LEDs 160, 162, 164 and 166 may include a Fairchild p/n QRD1114 consisting of a combined infrared LED/photodetector 167. The sensor pulley 134 includes alternating sectors of absorbent surfaces 148 and reflective surfaces 150 for absorbing or reflecting the infrared light emitted from the infrared LED/photodetector 167. The sensor pulley 134 may be constructed of a black ABS pulley wheel 135 and have a nominal radius 45 mm. The alternating sectors of absorbent surfaces 148 and reflective surfaces 150 may be constructed by masking the black ABS pulley wheel 135 and spraying a white paint into the voids of the mask. Alternatively, a pad-printing may be used to apply the alternating sectors of absorbent surfaces 148 and reflective surfaces 150 to the sensor pulley 134. The number of both absorbent surfaces 148 and reflective surfaces 150 positioned on infrared LED/photodetector 167 may include eighteen (18) wherein both absorbent surfaces 148 and reflective surfaces 150 have a width of 7.85 mm. The four infrared LED/photodetectors 167 are utilized at phase angles of 0, 45, 90 and 135 degrees and are placed at an angular spacing of 22.5 degrees to provide reliable position encoding with an angular resolution of 2.5 degrees.

The postscript program 168 to generate and tune a 36 half-element (number of alternating black and white surfaces) wherein the sensor pulley 134 has a nominal radius of 45 mm may include the following:

```
%! Postscript utility for printing an encoder wheel
%
/inch {72 mul} def    % #points/inch (don't change me)
/od 3.55 inch def     % outside diameter of wheel
/id 0.81 inch def     % inside diameter of wheel (hub)
/sod 3.55 inch def    % outside diameter of segments
/sid 2.75 inch def    % inside diameter of segments
/orad od 2 div def
/irad id 2 div def
/sorad sod 2 div def
/sired sid 2 div def
/segments 36 def   % number of segments (black and white)
/angle 360 segments div def
/wedge
{/radius exch def
/angle_s exch def
/angle_e exch def
newpath
% 0 0 moveto
0 0 radius angles_s angle_e arc
0 0 sired angle _e angle_s arc
closepath
}def
/circle
{
    /radius exch def
    newpath
    0 0 radius 0.360. arc
    closepath
} def
gsave
4.0 inch 4.0 inch translate
0 1 segments {
360 segments div rotate
angle 0 sorad wedge
2mod 0 eq{1}{0}ifelse
setgray fill
} for
0 setgray
0.5 setlinewidth
irad circle stroke
orad circle stroke
grestore
showpage
```

The sensor decoding 169 of the sensor 130 for measuring a displacement and a speed of the linkage 80 may be processed by using an Atmel ATF750CL-15 Complex Programmable Logic Device (CPLD) having the following equations:

```
Name Decoder8;
PartNo QD001;
Date 9/22/2004;
Revision 01;
Designer INW:
Company Inwoods Consulting;
Assembly AHF-003;
Location U8;
Device V750C;
/*************** INPUT PINS ********************/
PIN 1= Clk;              /* 6MHz input Clock */
PIN 2= Rest;             /* Reset */
PIN 3= DO;               /* Phi 0 degrees*/
PIN 4= D1;               /* Phi 45 degrees */
PIN 5= 02;               /* Phi 90 degrees */
PIN 6= D3;               /* Phi 135 degrees */
/*************** OUTPUT PINS ********************/
PIN 14= tCount;          /* Toggle Count*/
PIN 15= Up;              /* Up pulses, for internal use */
```

-continued

```
PIN 17= pCount;            /* un-delayed Count */
PIN 18= DIR;               /* Direction 1 = Up, 0 = Down */
PIN 19= Count;             /* Pulse count output*/
PIN 20= QDO;               /* Phi 0, delayed 2 DCLK*/
PIN 21= QD1;               /* Phi 45, delayed 2 DCLK */
PIN 22= QD2;               /* Phi 90, delayed 2 DCLK*/
PIN 23= QD3;               /* Phi 135, delayed 2 DCLK */
/*
** PINNODE 25..34 for Q1 of pins 14..23
** PINNODE 35..44 for Q0 of pins 14..23 (i.e. I/0 pins)
*/
PINNODE 25 = DCLKO;
PINNODE 27 = DCLK1;
PINNODE 37 = DCLK2;
PINNODE 31 = Q0; /* Phi 0, delayed 1 DCLK, buried register */
PINNODE 32 = 01; /* Phi 45, delayed 1 DCLK, buried register */
PINNODE 33 = 02; /* Phi 90, delayed 1 DCLK, buried register */
PINNODE 34 = Q3; /* Phi 135, delayed 1 DCLK, buried register */
/** Declarations and Intermediate Variable Definitions **/
/* Equations*/
/* Timing States */
DCLK2.t = DCLK1 & DCLKO;
DCLK1.t = DCLKO;
DCLKO.t = 'b'1;
[DCLK2..0].ckmux = Clk;
[DCLK2..0).ar = !Rest;
[DCLK2..0).sp ='b'0;
TO = !DCLK2 & !DCLK1 & !DCLKO;
T1 = !DCLK2 & !DCLKI & DCLKO;
T2 = !DCLK2 & !DCLK1 & !DCLKO;
T3 = !DCLK2 & DCLK1 & DCLKO;
T4 = DCLK2 & !DCLK1 & !DCLKO;
T5 = DCLK2 & !DCLK1 & DCLKO;
T6 = DCLK2 & DCLK1 & !DCLKO
T7 = DCLK2 & DCLK1 & DCLKO;
/* Latch the phase inputs on TO */
[Q3..0].ar = !Rest;
[O3..0].sp = 'b'0;
[Q3..0].ck = T7;
QD0.d = QO;
QD1.d = Q1;
QD2.d = Q2;
QD3.d = Q3;
/* Clock the latched inputs on T7, giving time for edge detection */
[QD3..0].ar = !Rest;
[QD3..0].sp ='b'0;
[QD3..0].ck = T7;
QD0.d = Q0;
QD1.d = Q1;
QD2.d = Q2;
QD3.d = Q3;
\* Edge Detection, sample for falling edges on T1 and rising edges on T3
*/
D0low = (!Q0 & !QD0);
D0high = (Q0 & QD0);
D0rise = (Q0 & !QD0 & T3);
D0fall =(!Q0& QD0&T1);
D1low= (!Q1 & !QDI);
D1high = (Q1 & QD1);
D1rise = (Q1 & !QD1 & T3);
D1fall = (!Q1 & QD1 & T1);
D2low = (!Q2 & !QD2);
D2high = (Q2 & QD2);
D2rise = (Q2 & !QD2 & T3);
D2fall= (!Q2 & QD2 & T1
D3low = (!Q3 & !QD3);
D3high = (Q3 & QD3);
D3rise = (Q3 & !QD3 & T3);
D3fall = (!Q3 & QO3 & T1);
/* Output a "Count" Pulse for edge edge detected */
pCount.ck = Clk;
pCount.sp ='b'0;
pCount.d = (D0rise # D1rise # D2rise #D3rise # D0fall # D1fall # D2fall
#D3fall);
pCount.oe = 'b'1;
pCount.ar=!Rest;
Count.ck = Clk;
Count_sp = 'b'0;
Count.d = pCount;
Count.oe = 'b'1;
Count.ar = !Rest;
/*Toggie Count - good for debug */
tCount.ar = !Rest;
tCount.sp = 'b'0;
tCount.ck = Count;           /*Toggie output on Count*/
tCount.d = !tCount
/*Direction - Define 8 states that are identified with the "UP" direction */
S0 = D0rise & D1low;
S1 = D0high & D1 rise & D2low;
S2 = D1high & D2rise & D3low;
S3 = D2high & D3rise;
S4 = D0fall & D1high;
S5 = D0low & D1fall & D2high;
S6 = D1 low & D2fall & D3high;
S7 = D2low & D3fall;
Up =(SO#S1 #S2#S3#S4#S5#S6#S7);
Up.oe = 'b'1;
Up.ar = !Rest;
DIR.ck = pCount;
DIR.sp ='b'0;
DIR.d = Up;
DIR.oe ='b'1;
DIR.ar = !Rest;
```

Figure 15:
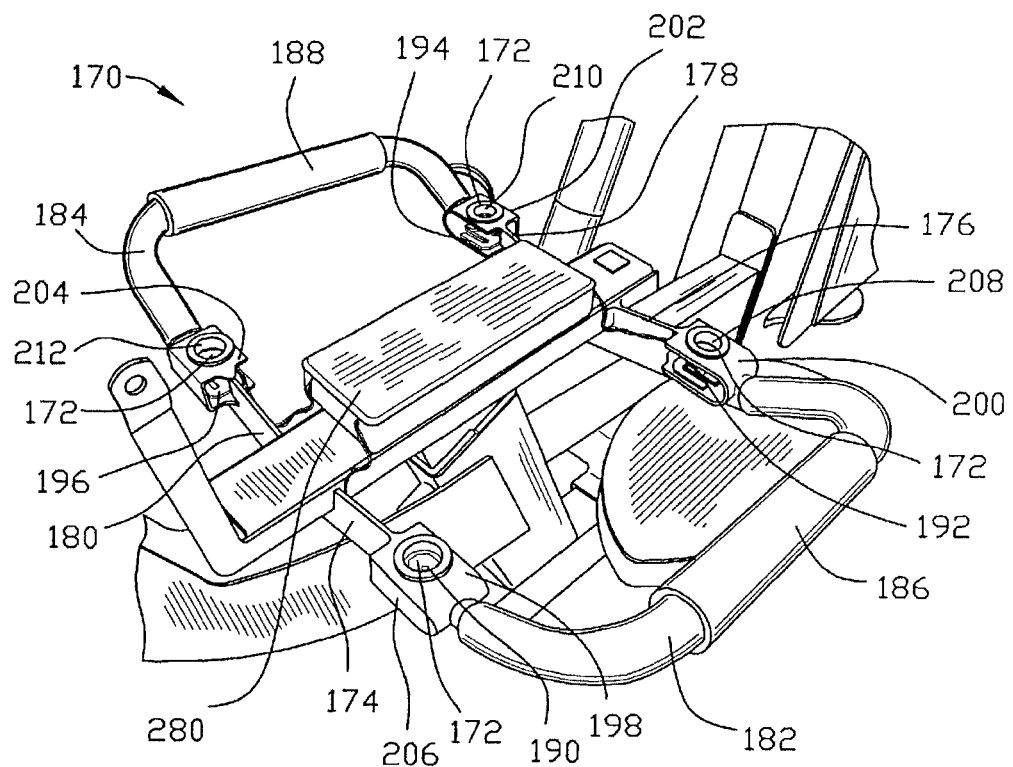
FIG. 15 is an isometric view of lower portion of FIG. 2 without a seat.
Figure 16:
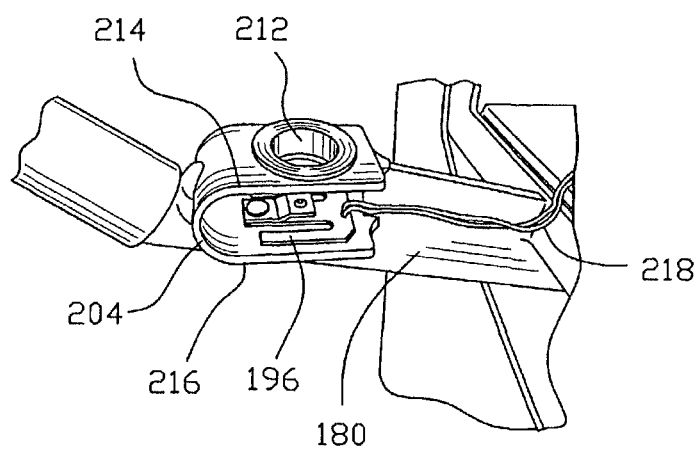
FIG. 16 is a magnified view of a portion of FIG. 14.

FIGS. 15-17 are views of a scale 170 for measuring a body weight of the operator 12. The scale 70 may comprises a plurality of strain gage load cell sensors 172. The seat 24 is secured to the frame 14 by a first, second, third and fourth seat support 174, 176, 178 and 180 extending from the lower frame unit 16. A first seat bar 182 having a first handle 186 may slidably engage the first and second seat support 174 and 176 for providing a body stabilizer for the operator 12. Similarly, a second seat bar 184 having a second handle 188 may slidably engage the third and fourth seat support 178 and 180 for providing a body stabilizer for the operator 12. The first, second, third and fourth seat support 174, 176, 178 and 180 include a first, second, third and fourth channel 198, 200, 202 and 204 respectively. The first, second, third and fourth channels include an upper leg 214 and a lower leg 216. Each of the upper legs 214 of the first, second, third and fourth channels include a first, second, third and fourth aperture 206, 208, 210 and 212 respectively. A first, second, third and fourth strain gage load cell sensor 190, 192, 194 and 196 are positioned on the first, second, third and fourth lower leg 216 of the first, second, third and fourth channel 198, 200, 202 and 204 respectively. The seat 24 has a front seat surface 220 and a rear seat surface 222. A first and a second support 224 and 226 are positioned on the underside of the seat 24 and extend past the front seat surface 220. A first and second bridge 228 and 230 extend over the first and second support 224 and 226. The first bridge 228 includes a first and a forth rod 232 and 238 for slidably engaging through the first and fourth apertures 206 and 212 to rest upon the first and fourth strain gage load cell sensors 190 and 196, respectively. The second bridge 230 includes a second and third rod 234 and 236 for and second bridge 228 and 230 include a slidably engaging through the second and third apertures 208 and 210 to rest upon the second and third strain gage load cell sensors 192 and 196, respectively.

FIGS. 18 and 19 are views of a monitor or weight encoder 250 for determining the number of the plurality of weights 40 that well be displaced upon the press 50 being displaced by the operator 12. The monitor 250 may include a plurality of infrared LEDs 257 and a plurality of optical sensors 258 positioned on a monitor plate 252. The monitor plate 252 includes a first and second anchor plate 254 and 256 for securing the monitor 250 adjacent to the lower frame unit 16. With the monitor plate 252 is positioned adjacent to the plurality of weights 40, as the pin 48 is inserted into horizontal weight cavity 46 of the plurality of weights 40 the light emitted from the infrared LED 257 is reflected back to the adjacent optical sensor 258 to product an electrical current.

The monitor 250 also includes a plurality of signals 260 for receiving an electrical current. The plurality of signals 260 instruct the operator 12 to place the pin 48 in one of the horizontal weight cavities 46 of the plurality of weights 40. The plurality of signals 260 may include a plurality of Bi-Color LED lights 262. A Bi-Color LED light 262 will generate a flashing green color to instruct the operator 12 to place the pin 48 in the aligning horizontal weight cavity 46. If the operator 12 places the pin in the aligning horizontal weight cavity 46 adjacent to the flashing LED light 262, the LED light 262 will convert to a steady green color. If the operator 12 places the pin in an alternative horizontal weight cavity 46 which is not adjacent to the flashing LED light 262, the LED light 262 adjacent to the pin will generate a steady red color. The monitor 250 also includes a plurality of weight values 264 to provide the operator 12 with the load value the operator 12 will be displacing upon displacement of the press 50.

Figure 20:
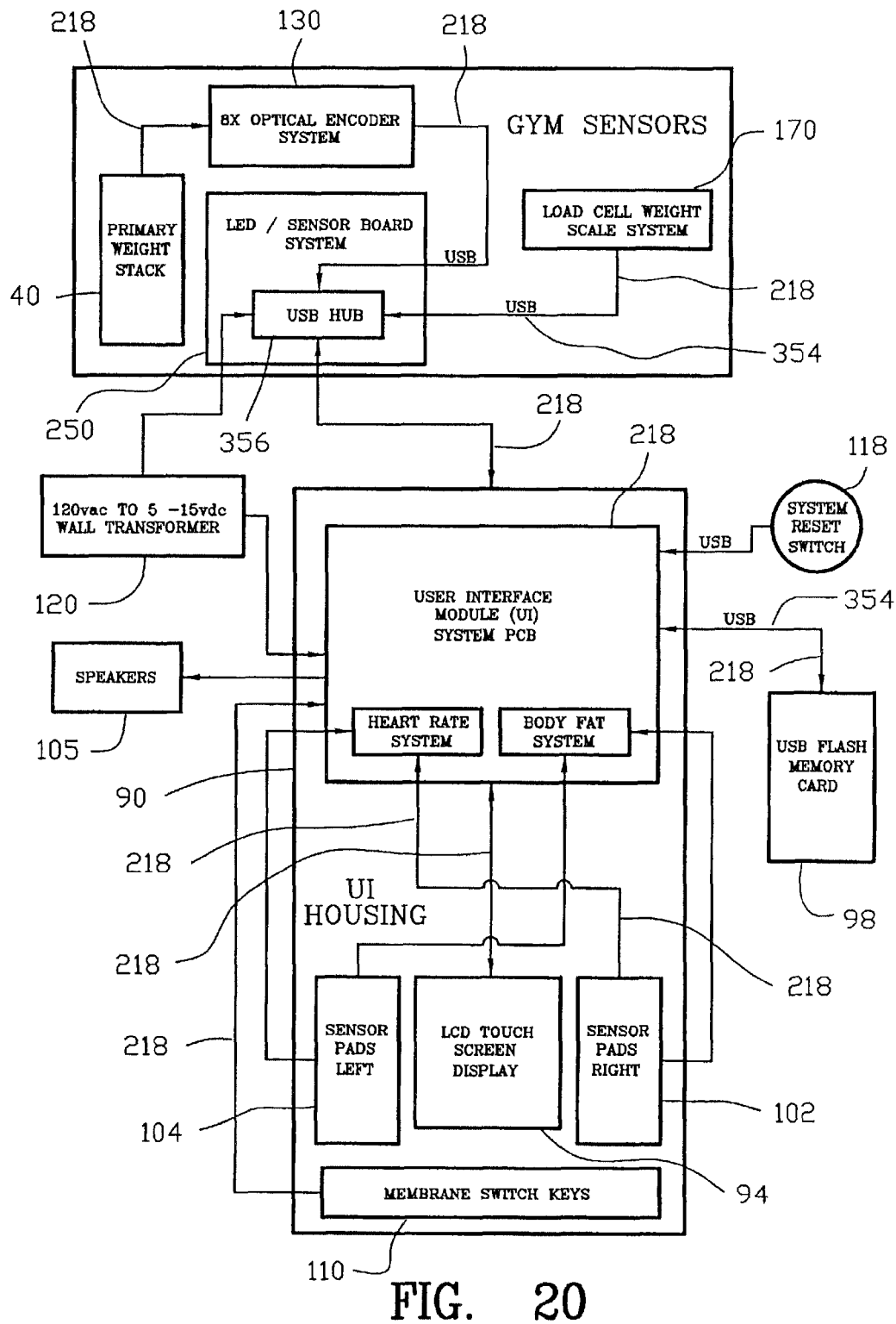
FIG. 20 is a wire diagram of the electrical components of the apparatus for enabling the operator to exercise incorporating the present invention.

FIG. 20 is a wire diagram of the electrical components of the apparatus 10 for instructing the operator 12 thru an interactive exercise program. A user interface module (UI) 90 contains a printed circuit board (PCB) 280 containing a central processing unit (CPU) 350. The CPU 350 performs the arithmetic and logical operations, namely the data received from the sensor 130, scale 170, monitor 250, the liquid crystal touch screen display 94 and memory storage 96. The PCB 280 also contains read only memory (ROM) 352 for storing software programs. The software programs instruct the operator 12 thru an interactive exercise program that monitors the operator's exercise program progress, provides exercise tips, records the operator's personal data and fitness program results and exports the operator's data to a memory storage 96. The PCB 280 is in electrical communication with the liquid crystal touch screen display 94, sensor 130, scale 170, contact 100, monitor 250, and memory storage 96 by a plurality of wires 218. The electrical communication between the PCB 280 and liquid crystal touch screen display 94, sensor 130, scale 170, contact 100, monitor 250, and memory storage 96 may include a Universal serial bus (USB) interface system 354.

More specifically, the PCB 280 communicates with the liquid crystal touch screen display 94 for providing exercising instructions to the operator 12. The operator 12 may input data from the liquid crystal touch screen display 94 to the PCB 280. The PCB 280 also receives data from the sensor 130 for processing the performance of the exercising instruction by the operator 12. The sensor 130 monitors any movement of the sensor pulley 134. The CPU 350 converts this movement into speed and direction data. The speed and direction data is displayed on the liquid crystal touch screen display 94 to provide an on-screen visual display of the speed and direction data of the plurality of weights 40 in real-time. This visual display may be beneficial for practicing the correct rate and pace for a particle exercise.

The PCB 280 receives data from the scale 170 for processing the weight of the operator 12. The scale 170 includes first, second, third and fourth strain gage load cell sensors 190, 192, 194 and 196 that are incorporated into the seat 24. The PCB 280 interprets and integrates the strain gage load cell sensors signals. The scale data is displayed on the liquid crystal touch screen display 94 and is stored on the memory storage 96 to record the operator's weight. The PCB 280 further receives data from the contact 100 for processing the heart rate and the body fat of the operator 12. The contact 100 is incorporated into the user interface module 280. The contact 100 provides sensor input to the PCB 280. The contact data is displayed on the liquid crystal touch screen display 94 and is stored on the memory storage 96 to record the operator's heart rate and body fat. The stored heart rate and body fat data is used to track the health of the operator 12.

The PCB 280 further receives data from the monitor 250 for processing the number of plurality of weights 40 displaced by the operator 12. The monitor 250 includes a plurality of infrared LED 257 aligned with a plurality of optical sensors 258 adjacent to each of the plurality of weights 40. The monitor 250 provides sensor input to the PCB 280 as to the position of the pin 48 upon the pin 48 blocking the light emitting from the infrared LED 257 to the optical sensor 258. The plurality of weight data is displayed on the liquid crystal touch screen display 94 and is stored on the memory storage 96 to record the weight lifted by the operator 12. The monitor 260 also includes a plurality of signals 260 comprising a bio-colored LEDs 262 adjacent to each of the plurality of weights 40. The software calculates the proper weight for the operator's program. The PCB 280 transmits a signal to the monitor 260 to illuminate the bio-colored LED 262 adjacent the proper weight. The illuminated bio-colored LED 262 provides a visual indication to the operator 12 regarding the pin 48 placement for an exercise. The normal condition the bio-colored LED 262 is not illuminated. When the software program sends a signal to the proper plurality of weights 40 for the operator's program, the bio-colored LED 262 will illuminate a flashing green signal to inform the operator 12 in which plurality of weights 40 to insert the pin 48. When the operator 12 has properly placed the pin 48 adjacent to the flashing green bio-colored LED 262, the optical sensor 258 senses the location of the pin 48 and will send a corresponding signal back to the PCB 280 as confirmation. The software program will then send a response signal back to the bio-colored LED 262 and turn the bio-colored LED 262 to steady green to notify the operator 12 that they have the pin 48 in the proper position for the exercise.

If the operator 12 elects to not place pin 48 in the recommended position, and places the pin 48 in an alternate position, the optical sensor 258 at the alternate position will send a signal to the PCB 280 of the alternative selection and in turn generate a pop-up notice on the liquid crystal touch screen display 94 and also send a signal to the bio-colored LED 262 at the alternate position and create a flashing red signal. The bio-colored LED 262 that was recommended for the pin 48 location will continue to flash green. If the operator 12 confirms the use of the alternate pin 48 location by interacting with the liquid crystal touch screen display 94, the software will send an appropriate signal to the alternate position of the bio-colored LED 262 and create a steady green bio-colored LED 262 condition and extinguish the bio-colored LED 262 at the recommended position. At the same time the software will change the operator's program to use the alternate position for the exercise program.

The PCB 280 receives data from both the sensor 130 and the monitor 250 thru a USB Hub system 356 that is integrated into a monitor PCB board. The user interface module 90 may also includes an audio system 106, a system reset switch 118. The audio system 105 has a first speaker 106 and a second speaker 108 that produces feedback tones during the operator's interaction with the apparatus 10. The PCB 280 may be powered by a wall transformer 120 wherein the 120 vac is converted to 5-15 vdc.

The PCB 280 further transfers data to the memory storage 96 for saving the weight and the heart rate and the body fat of the operator 12 and the number of plurality of weights 40 displaced and the performance of the exercising instruction by the operator 12. The memory storage 96 is inserted into the input port 95 located on the face of the user interface module 90. The memory storage 96 allows the apparatus 10 to acknowledge individual operators 12 and for the operator 12 to record and analyze individual personal data after the exercise session is completed. The memory storage 96 may include a removable memory device 98. The function of the removable memory device 98 may include acting as an ignition key to start the application software and load personal data and exercise programs into the user interface module 90, acting as a repository of personal operator data and exercise program data that can be removed and reinserted into any gym having an apparatus 10 to automatically load the appropriate personal operator data and continue the operator's exercise program. The removable memory device 98 may also function to allow the operator 12 to access and print out the operator's daily exercise results on a system located in a exercise facility, to permit the operator 12 to upload the operator's data to the a common Website for remote access via password encryption and permit connection to the World Wide Web and uploads data that will be used by the manufacture to populate a Global Database with information such as: Gender, Age, Height, Weight, Strength Test Results, Body Fat, Heart Rate, Resting Metabolic rate, Exercise Program Information, Program intensity Factors, Etc.

Figure 21:
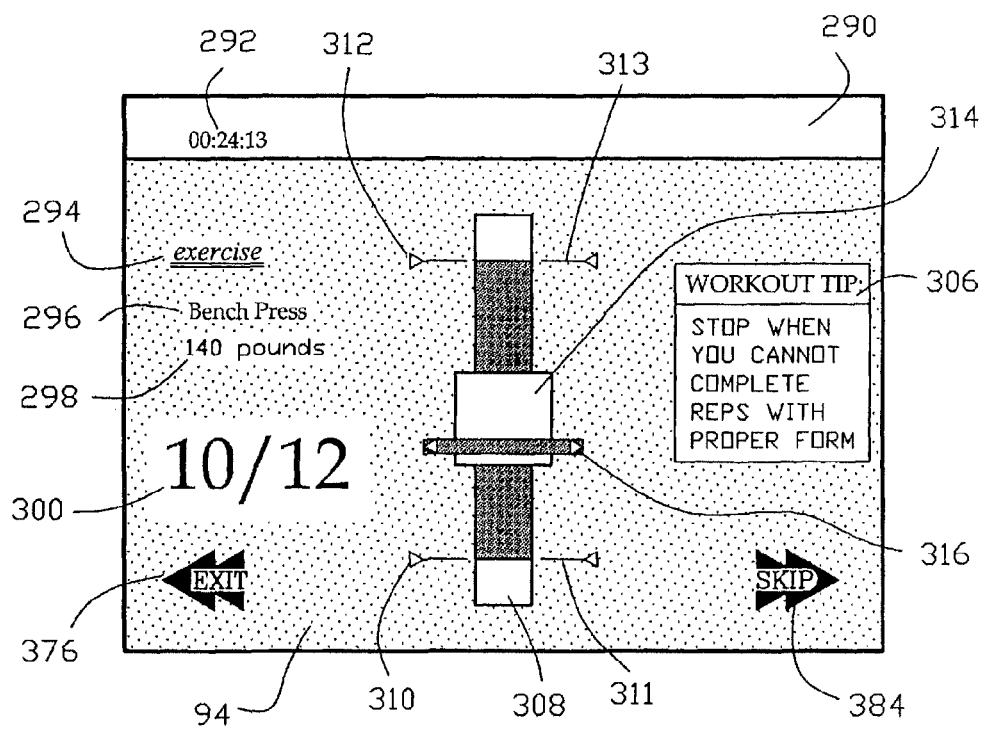
FIG. 21 is a visual image displayed on the display.
Figure 22:
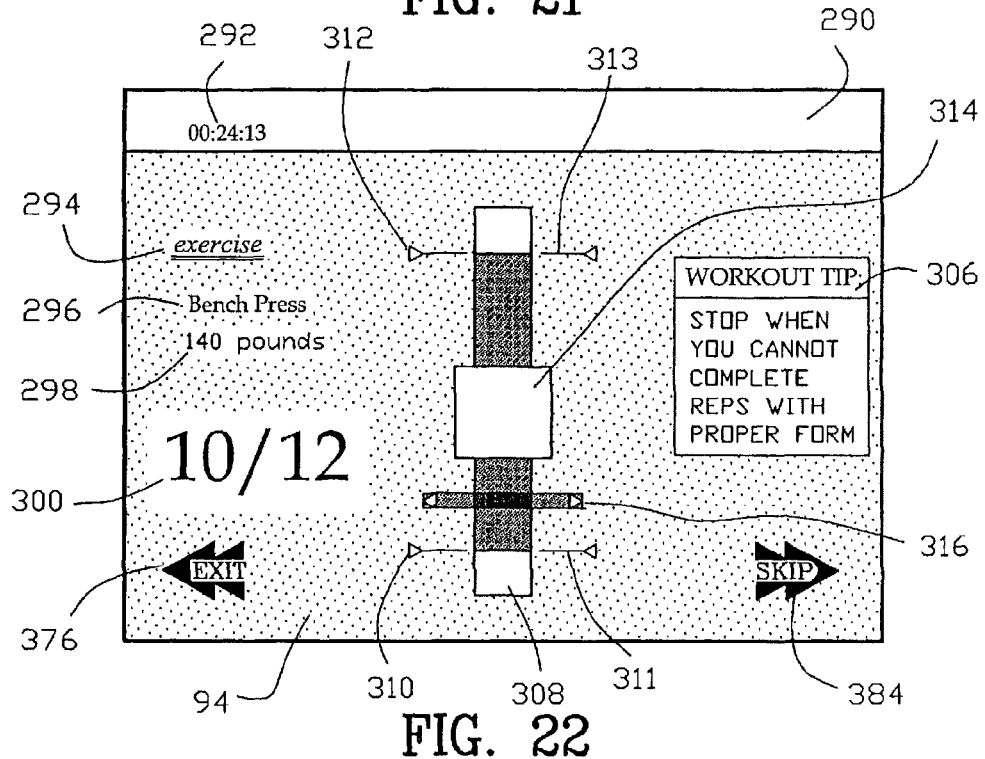
FIG. 22 is a view similar to FIG. 21.

FIG. 21 illustrates the PCB 280 transferring data to the liquid crystal touch screen display 94 for providing an exercise instruction to the operator 12. The exercising instruction 294 provided by the PCB 280 to the liquid crystal touch screen display 94 may include visual data comprising the time 292, the press type 296, the weight value 298, and the number of executed reps 300. The exercising instruction 294 may also include visual data for illustrating the displacement and the speed of the linkage 80 with respect to a predetermined standard in real time. More specifically, the visual data includes a rate of executed exercise 308 including a lower range of exercise 310 and an upper range of exercise 312. As the operator 12 displaces the press 50 to displace the load 38, the sensor 130 relays the displacement and the speed of the linkage 80. The PCB 280 then relays a graphical image of the displacement and the speed to the liquid crystal touch screen display 94. The displacement and speed of the linkage 80 is visually displayed by the operator pace bar 316. The PCB 280 provides an approximate programmed displacement and speed by a program pace bar 314. The operator 12 is to match the displacement and speed of the press 50 with the displacement and speed of the program pace bar 314. FIG. 22 illustrates the operator pace bar 316 outside the recommended program pace bar 314. In this event, the operator 12 would need to adjust the displacement and speed of the press 50 to match the displacement and speed of the program pace bar 314.

The exercising instruction 294 may further include an exercising notice 306 instructing the operator 12 to terminate exercising the current exercising instruction 294 once the operator 12 can not maintain the operator pace bar 316 within the program pace bar 314.

Figure 23:
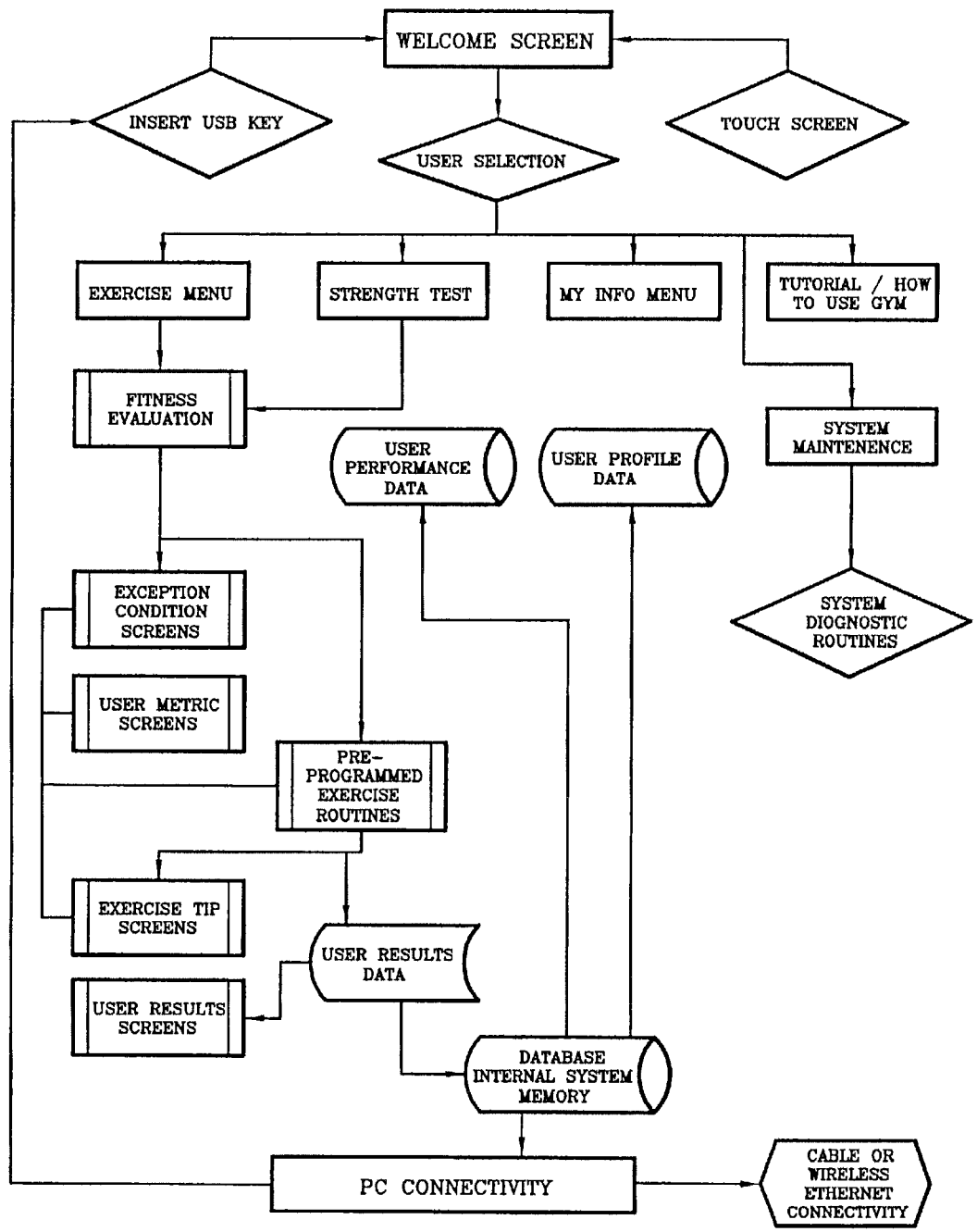
FIG. 23 is a flow chart of the process for utilizing the apparatus for enabling the operator to exercise incorporating the present invention.

FIG. 23 is a flow chart of the application software process for utilizing the apparatus 10 for enabling the operator 12 to exercise. FIGS. 24-41 illustrate the process of enabling an operator 12 to exercise incorporating the present invention, comprising the steps of inserting a memory storage into a processor for reading and storing data, providing an exercising instruction to the operator, processing the performance of the exercising instruction by the operator, and saving the performance of the exercising instruction by the operator on the memory storage. More specifically the process of enabling an operator to exercise may include the steps of inserting a removable memory device into a processor for reading and storing data, providing an exercising instruction to the operator, processing the performance of the exercising instruction by the operator, measuring the weight of the operator, measuring the heart rate and the body fat of the operator, counting the number of plurality of weights displaced by the operator, and saving the weight and the heart rate and the body fat of the operator and the number of plurality of weights displaced and the performance of the exercising instruction by the operator on the removable memory device.

Figure 24:
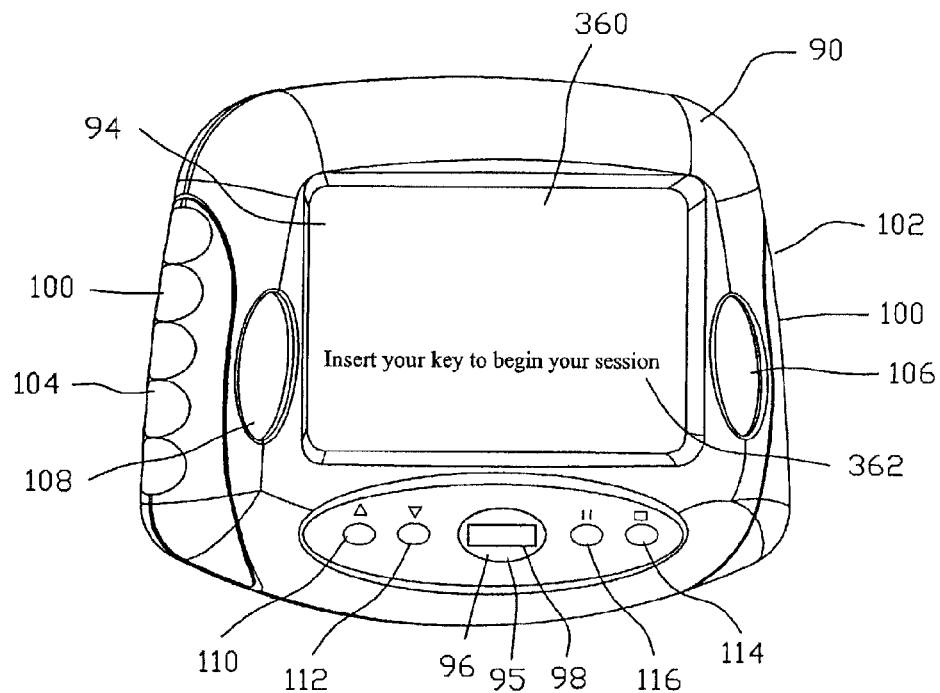
FIG. 24 is an enlarged view similar to FIG. 9.

FIG. 24 illustrates the liquid crystal touch screen display 94 of the user interface module 90 displaying a welcome screen 360. The welcome screen 360 include welcome text 362 instructing the operator 12 to insert the removable memory device 98 into the input port 95 to begin the operator's exercise program.

Figure 25:
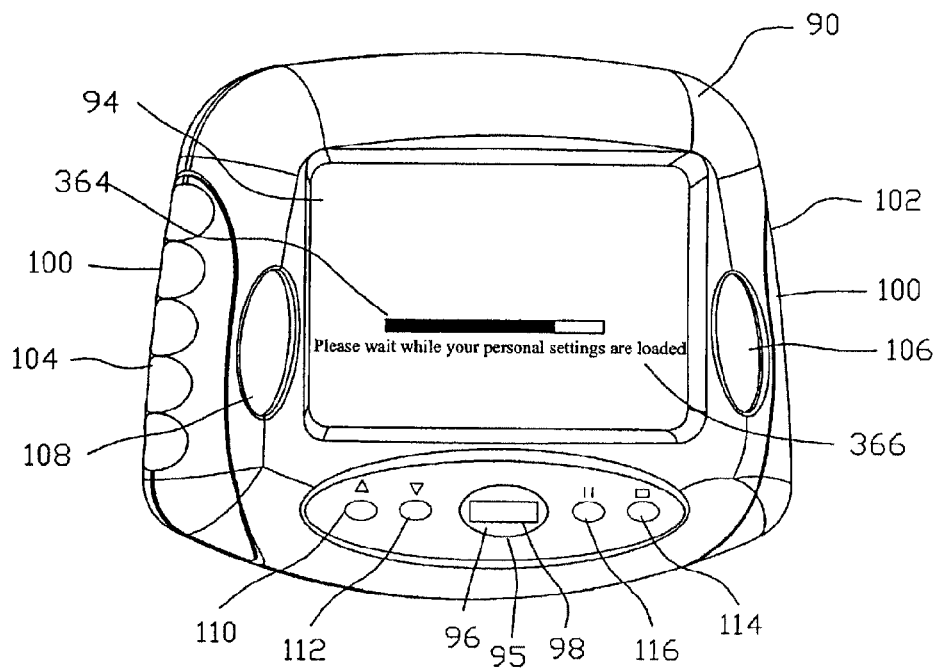
FIG. 25 is an enlarged view similar to FIG. 9.

FIG. 25 illustrates the liquid crystal touch screen display 94 displaying a data loading bar 364 and loading text 366 instructing the operator 12 to wait for data to be loaded. The insertion of the removable memory device 98 starts the application software and loads personal data and exercise programs into the user interface module 90.

Figure 26:
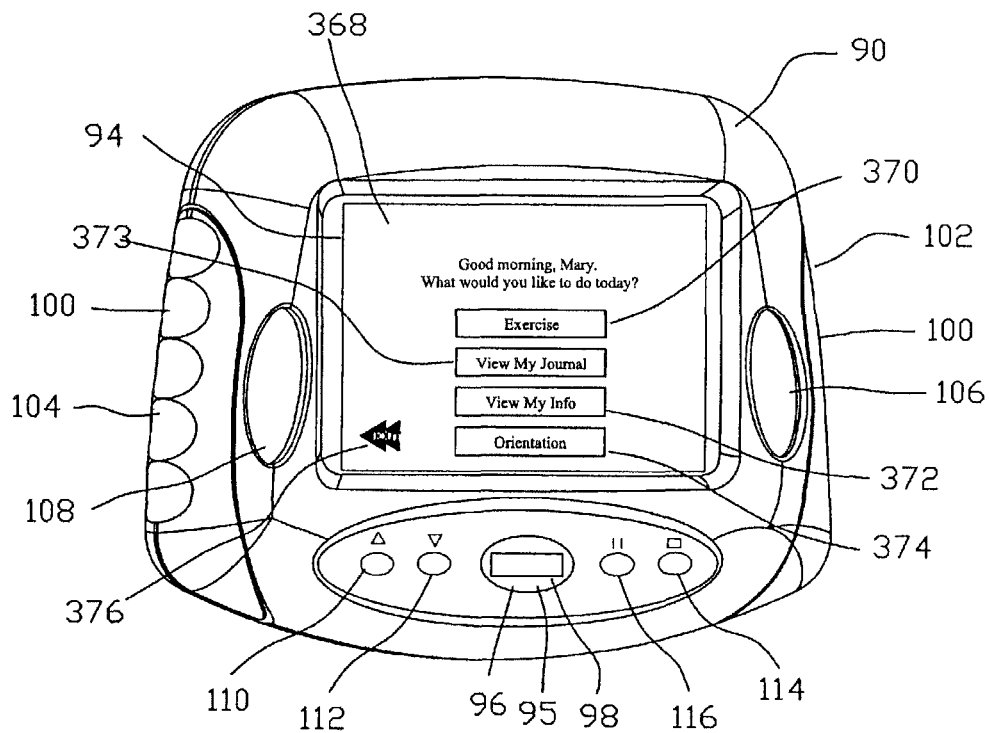
FIG. 26 is an enlarged view similar to FIG. 9.

FIG. 26 illustrates the liquid crystal touch screen display 94 displaying an option screen 368. The option screen 368 includes an exercise option 370 to begin exercising instructions, a journal option 372 to review the exercising history of the operator 12, a view information option 373 to review the operator's personal information and an orientation option 374 to review a tutorial on the operation of the apparatus 10. The option screen 368 also includes an exit function 376 to terminate the program.

Figure 27:
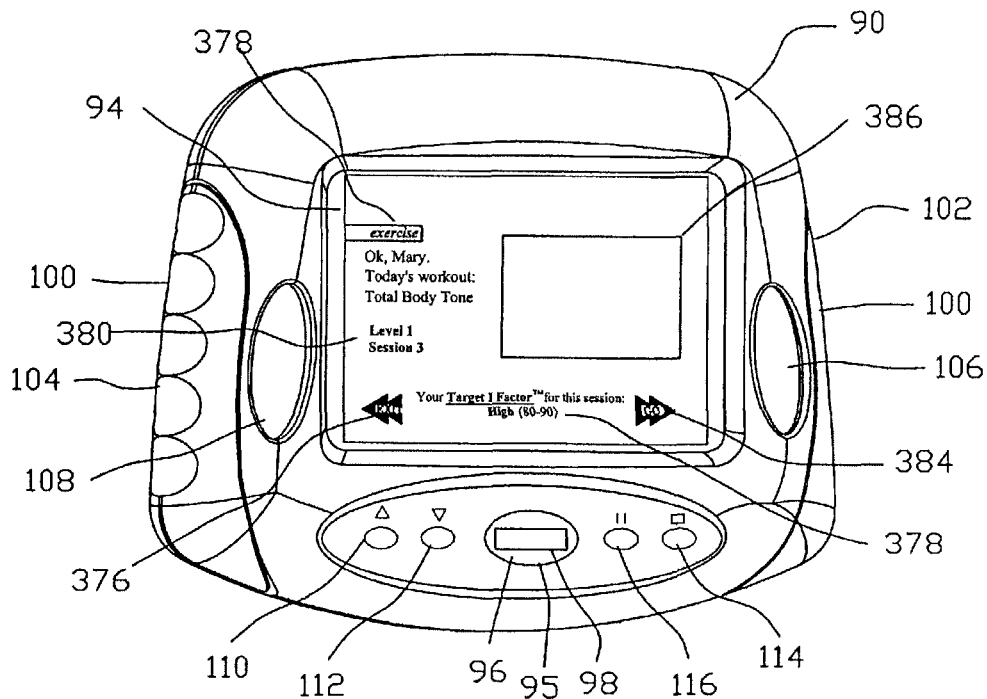
FIG. 27 is an enlarged view similar to FIG. 9.

FIG. 27 illustrates the liquid crystal touch screen display 94 displaying an exercising menu 378 to instruct the operator to begin utilizing the apparatus 10 to exercise. The exercising menu 378 includes an exercising intensity level indicator 380 to instruct the operator as to the difficult and number of the specific exercise. The exercising menu 378 also includes a target indicator 382 for disclosing an exercise parameter to be reached. The exercising menu 378 further includes a go function 384 for forwarding the program to the next exercise. The exercise menu 378 may also comprise an image portion 386 for displaying either a picture or a motion picture of an individual using the current exercise to illustrate the usage of the apparatus 10.

Figure 28:
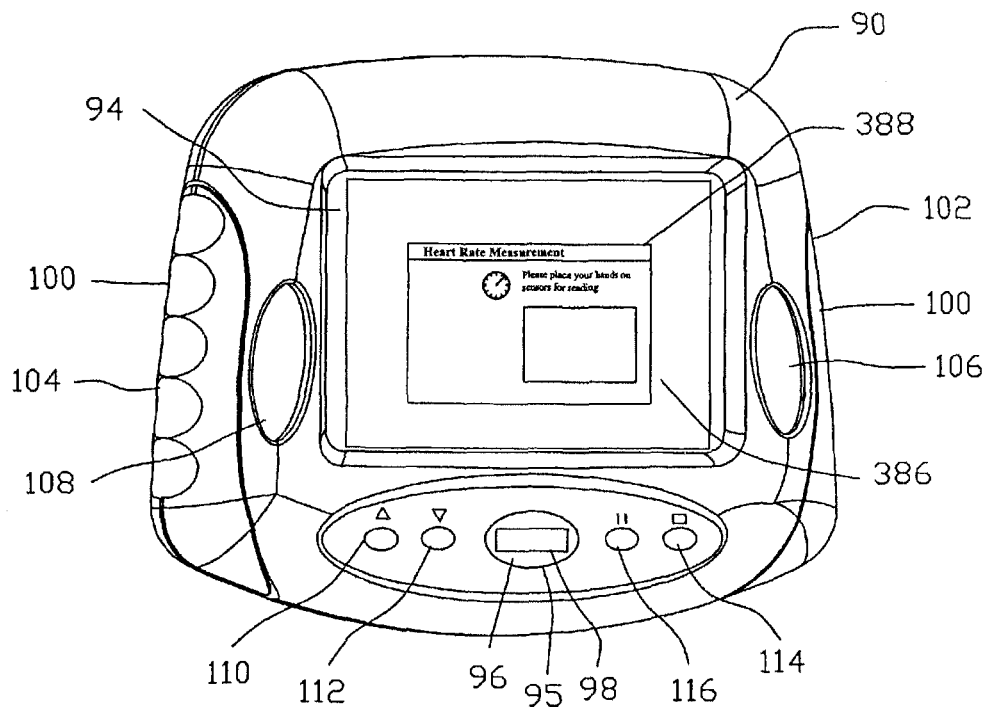
FIG. 28 is an enlarged view similar to FIG. 9.

FIG. 28 illustrates the liquid crystal touch screen display 94 displaying a heart rate menu 388. The heart rate menu 388 instructs the operator 12 to stop exercising and to place the operator's hands on the user interface module 280 with the hands contacting the first and second contact pads 102 and 104. The measuring of the operator's body fat is conducted similar to the measurement of the heart rate of the operator 12.

Figure 29:
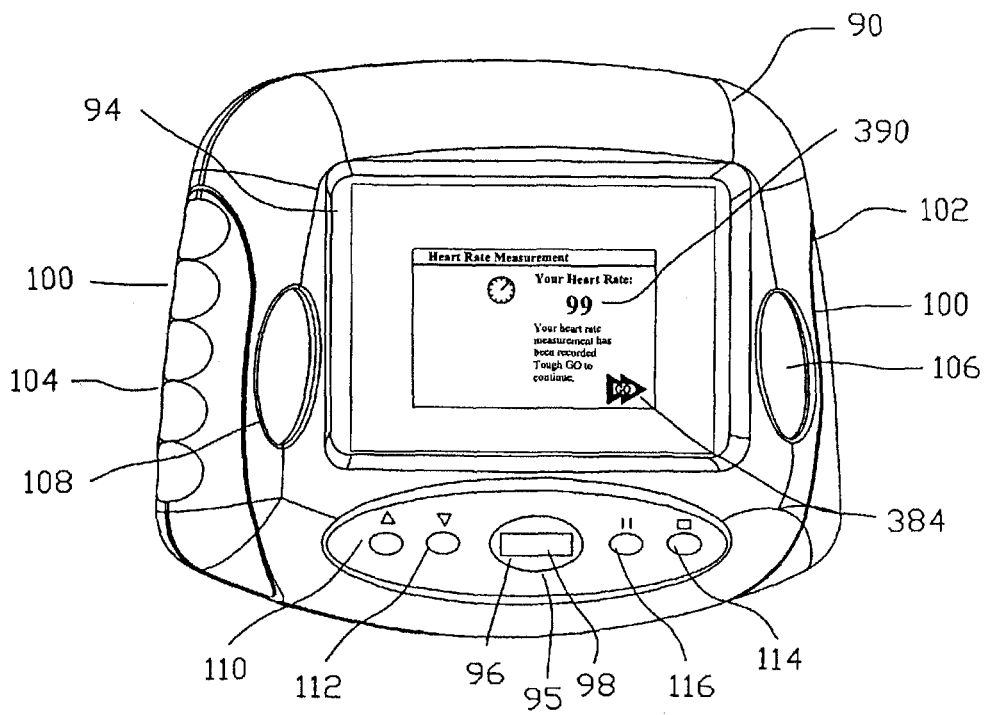
FIG. 29 is an enlarged view similar to FIG. 9.

FIG. 29 illustrates the liquid crystal touch screen display 94 displaying a heart rate menu 388. The heart rate menu 388 displays the operator's heart rate 390 and instructs the operator 12 to continue utilizing the apparatus 10 for exercising. The heart rate information is saves to the removable memory device 98.

Figure 30:
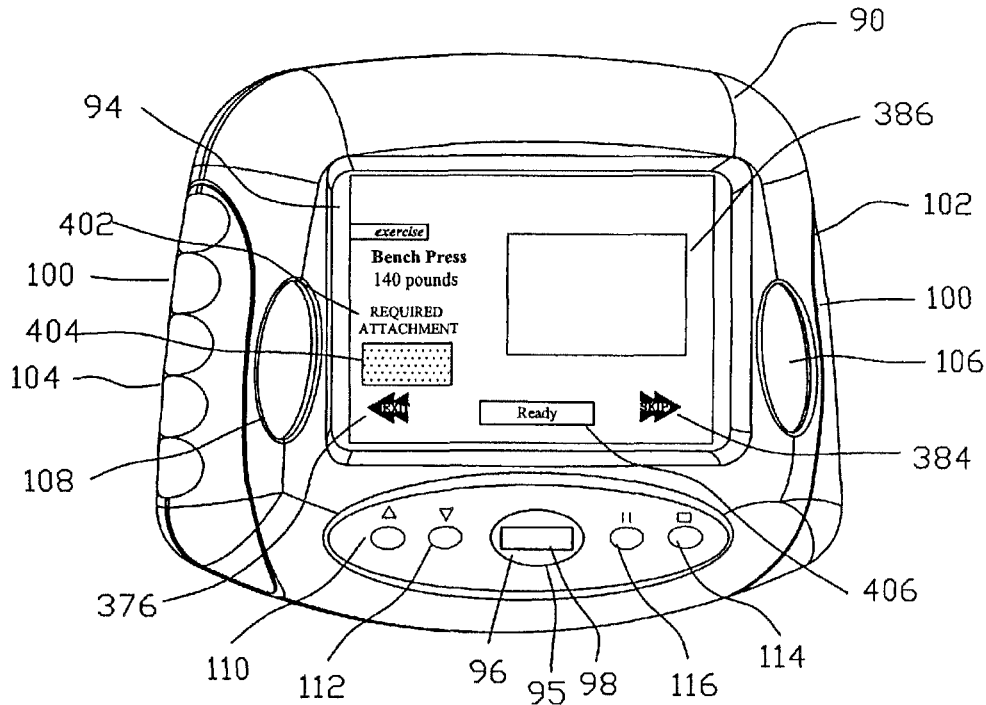
FIG. 30 is an enlarged view similar to FIG. 9.

FIG. 30 illustrates the liquid crystal touch screen display 94 displaying a second exercising menu 400 to instruct the operator 12 to begin utilizing the apparatus 10 to exercise. The second exercising menu 400 includes an attachment notification 402 for indicating an exercising attachment requirement for the next exercise. The attachment notification 402 may also include an image or motion picture of the exercising attachment 404. The second exercising menu 400 also includes a confirmation input 406 to confirm the exercising attachment is ready to be utilized.

Figure 31:
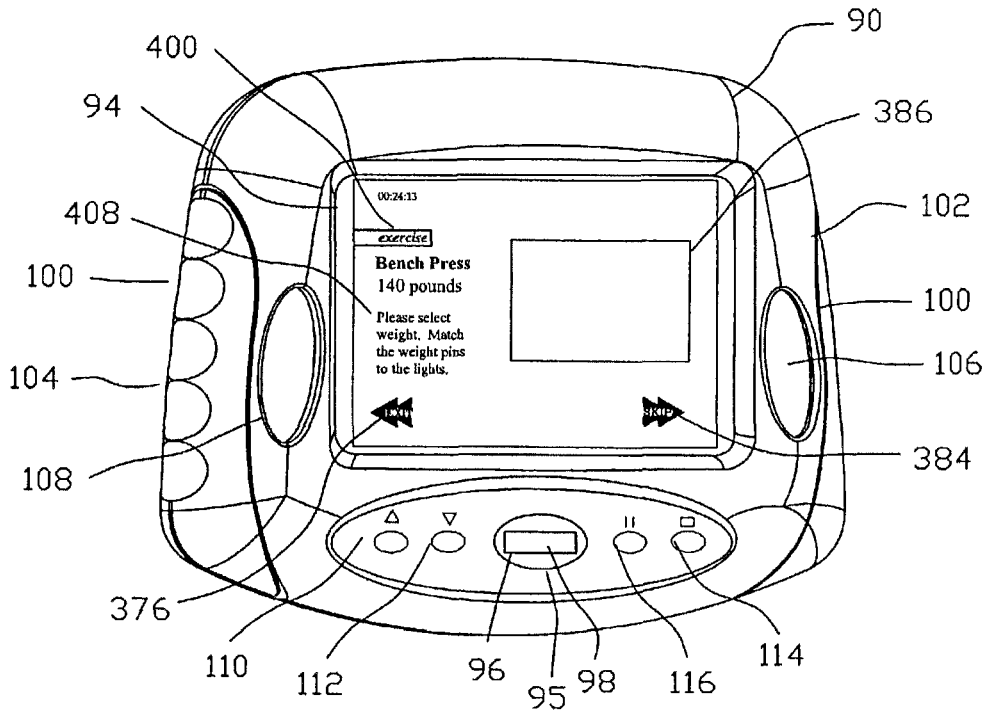
FIG. 31 is an enlarged view similar to FIG. 9.

FIG. 31 illustrates the liquid crystal touch screen display 94 displaying the second exercising menu 400 including a weight selection notification 408 to instruct the operator 12 to insert the pin 48 into one of the plurality of weights 40 which is adjacent to the flashing green bio-colored LED 262.

Figure 32:
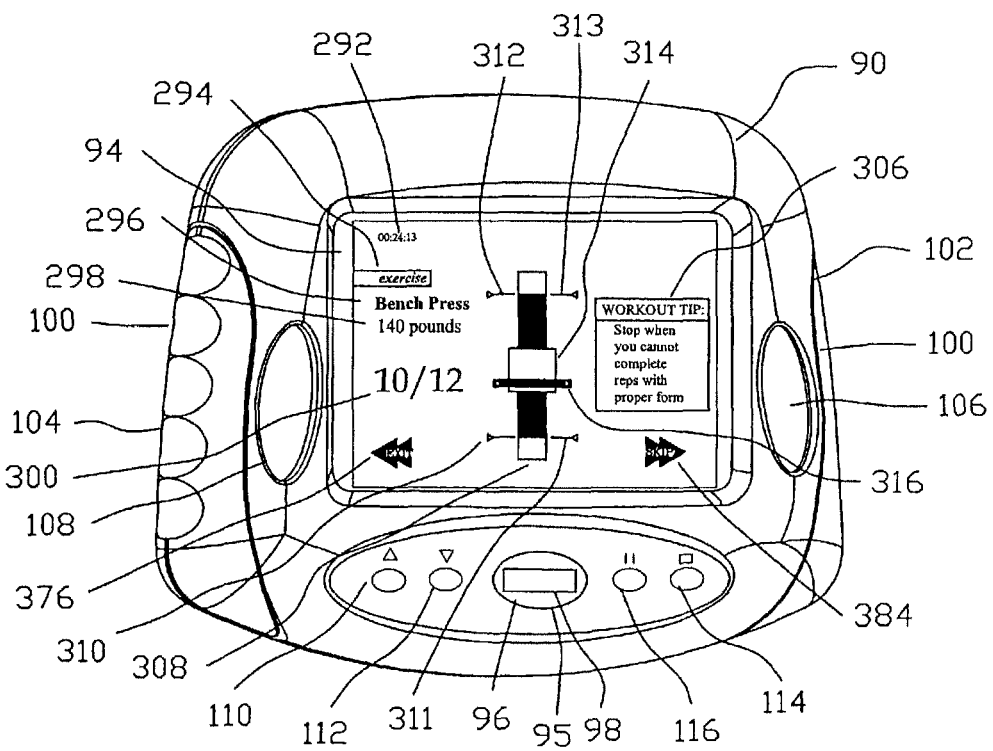
FIG. 32 is an enlarged view similar to FIG. 9.

FIG. 32 is similar to FIGS. 21 and 22 which illustrates the liquid crystal touch screen display 94 displaying visual data for illustrating the displacement and the speed of the linkage 80 with respect to a predetermined standard in real time. More specifically, the visual data includes a rate of executed exercise 308 including a lower range of exercise 310 and an upper range of exercise 312. The exercising instruction 294 may further include an exercising notice 306 instructing the operator 12 to terminate exercising the current exercising instruction 294 once the operator 12 can not maintain the operator pace bar 316 within the program pace bar 314.

Figure 33:
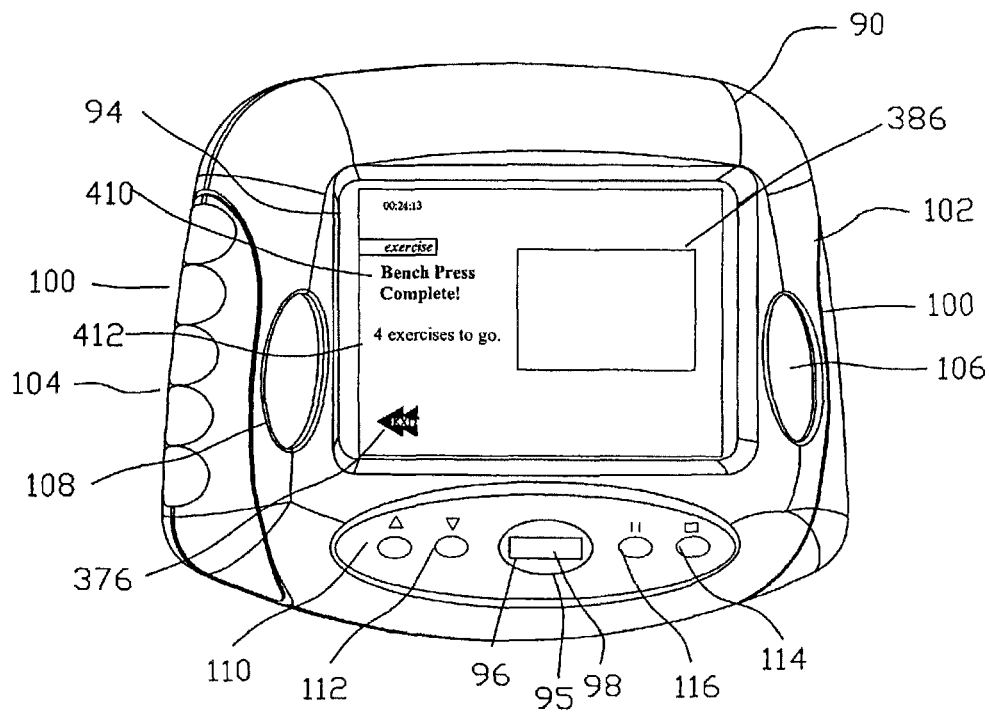
FIG. 33 is an enlarged view similar to FIG. 9.

FIG. 33 illustrates the liquid crystal touch screen display 94 displaying a termination menu 410 for a specific exercise. The termination of a specific exercise menu 410 including a notification of any remaining exercises to be completed 412.

Figure 34:
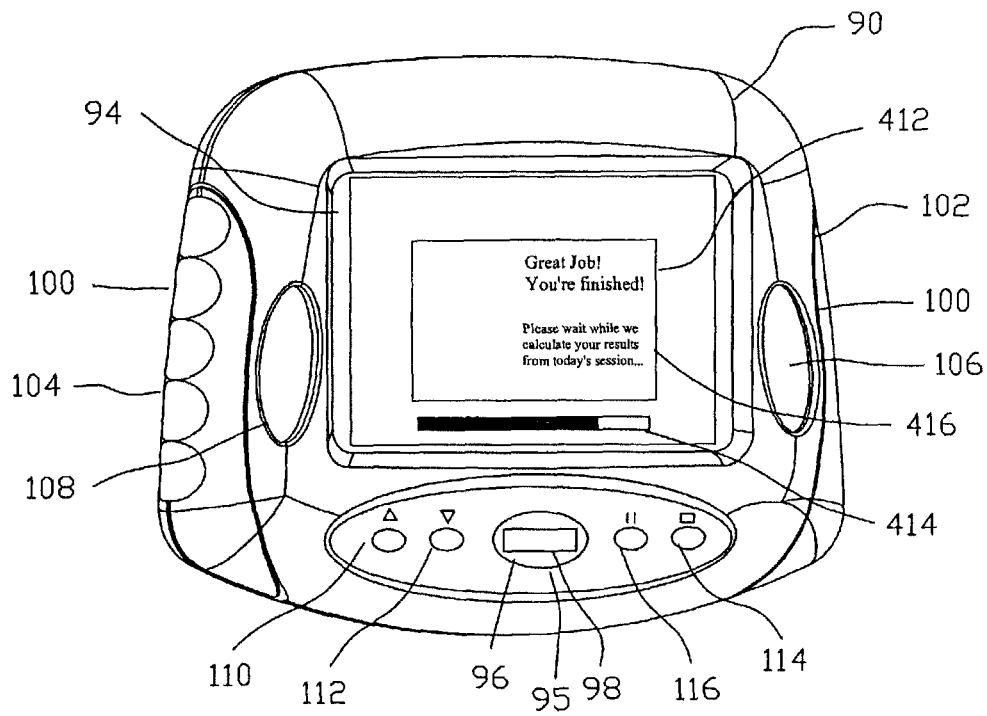
FIG. 34 is an enlarged view similar to FIG. 9.

FIG. 34 illustrates the liquid crystal touch screen display 94 displaying a second termination menu 412 indicating termination of all exercises. The second termination menu 412 includes a data calculating bar 414 and calculating text 416 instructing the operator 12 to wait for data to be calculated.

Figure 35:
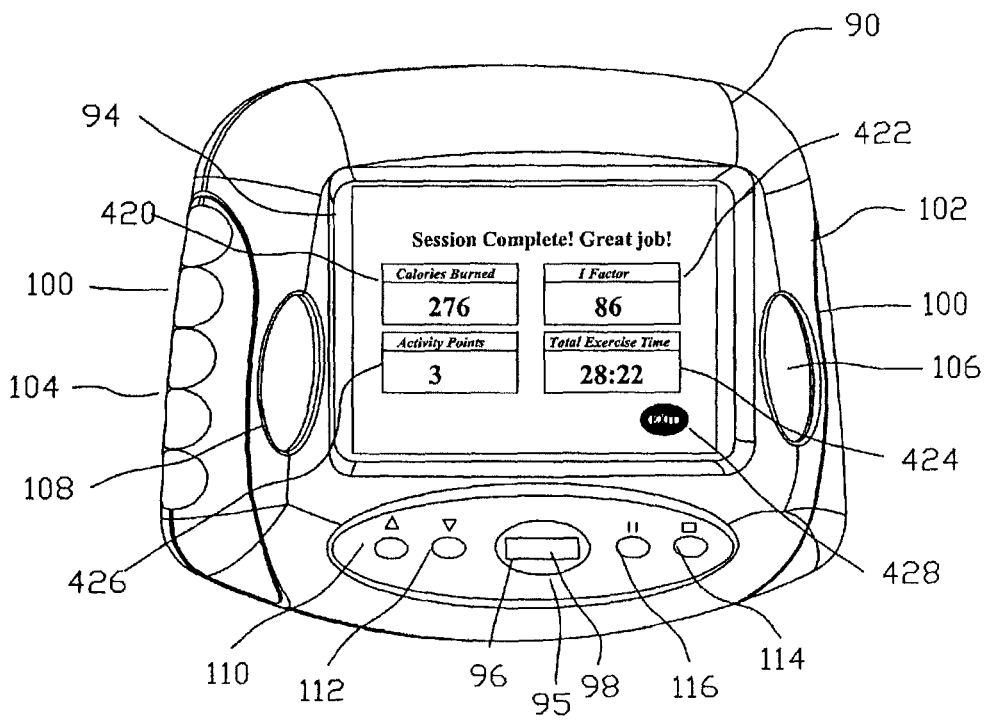
FIG. 35 is an enlarged view similar to FIG. 9.

FIG. 35 illustrates the liquid crystal touch screen display 94 displaying a performance menu 418. The performance menu 418 includes the calculations for calories burned 420, targeted heart rate 422, total exercise time 424 and points acquired 426 for the exercise session. The performance menu also includes an exit function 428 for terminating the performance menu.

Figure 36:
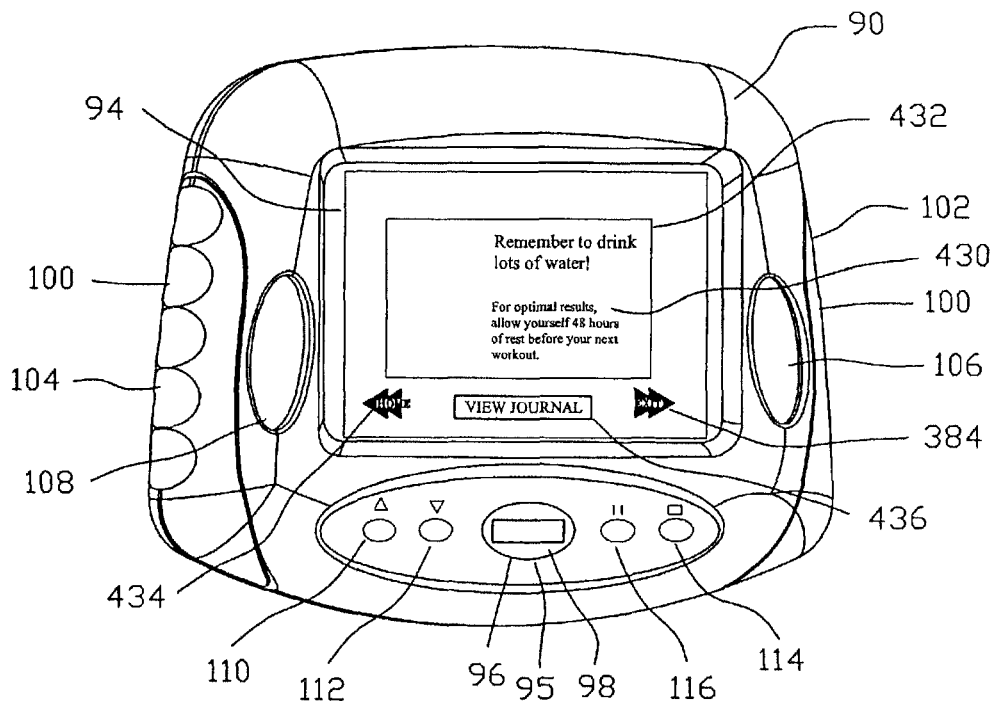
FIG. 36 is an enlarged view similar to FIG. 9.

FIG. 36 illustrates the liquid crystal touch screen display 94 displaying a scheduling menu 430 for the operator to return for the next exercise session. The scheduling menu 430 includes a notice 432 to include pertinent information such as to consume water after exercising. The scheduling menu 430 may also include a home function 434 and a journal function 436. The home function 434 returns the program to the main menu. The journal function 436 forwards the program to a journal menu.

Figure 37:
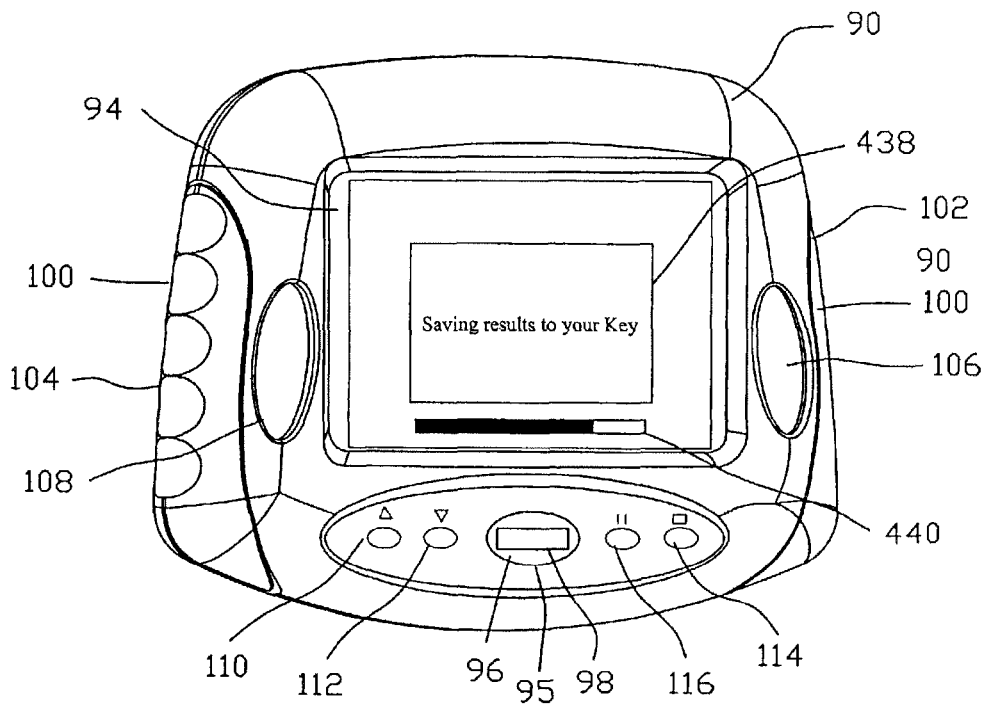
FIG. 37 is an enlarged view similar to FIG. 9.

FIG. 37 illustrates the liquid crystal touch screen display 94 displaying a saving menu 438 for indicating data being stored on the removable memory device 98. The saving menu 438 includes a storage bar 440 for instructing the operator 12 to wait for data to be stored on removable memory device 98.

Figure 38:
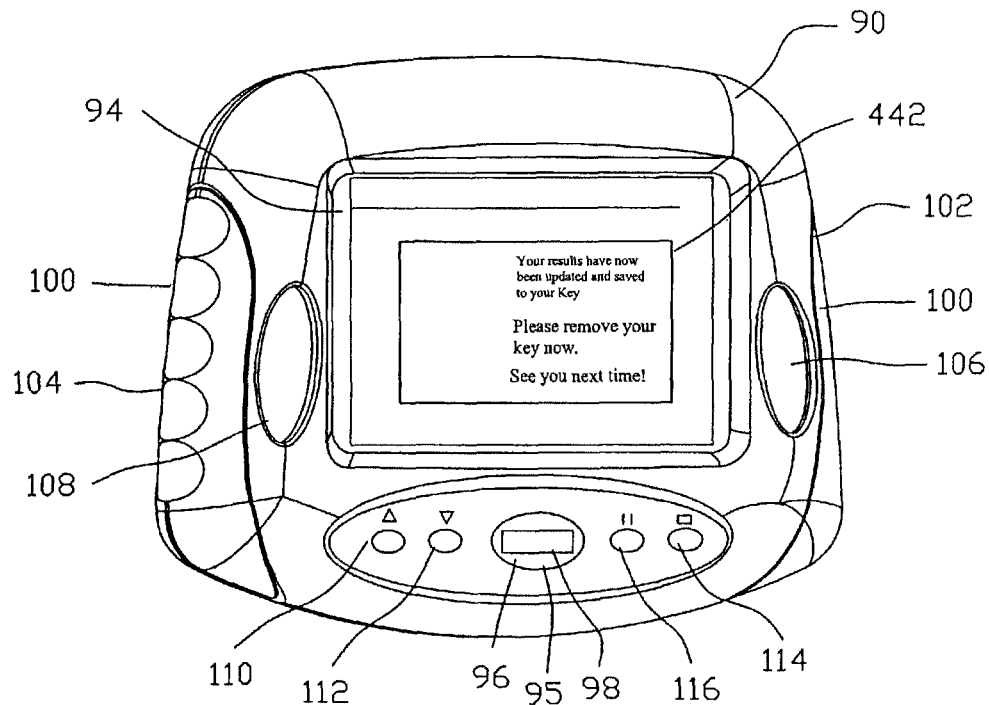
FIG. 38 is an enlarged view similar to FIG. 9.

FIG. 38 illustrates the liquid crystal touch screen display 94 displaying a conclusion menu 442 for instructing the operator 12 to remove the removable memory device 98.

Figure 39:
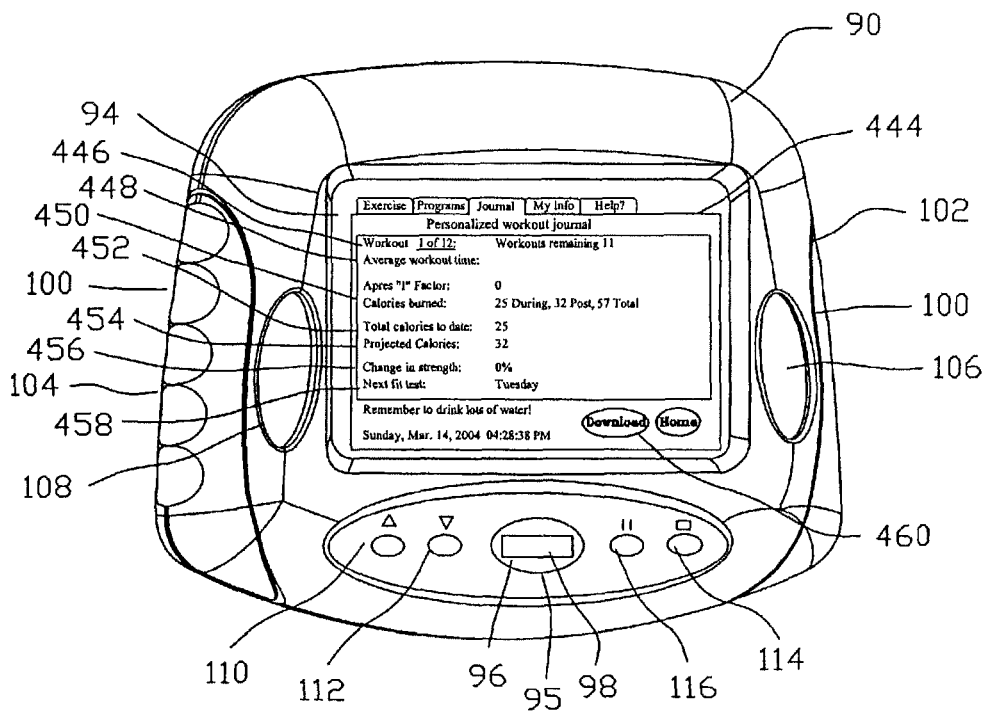
FIG. 39 is an enlarged view similar to FIG. 9.

FIG. 39 illustrates the liquid crystal touch screen display 94 displaying a first journal menu 444 including a review the exercising history and future exercise sessions to be conducted by the operator 12. The first journal menu 444 may comprise: number of workout 446, average workout time 448, calories burned 450, total calories to date 452, projected calories 454, change in strength 456, and next fit test 458. The first journal menu 444 may also include a download function 460 to transfer the journal data to the removable memory device 98.

Figure 40:
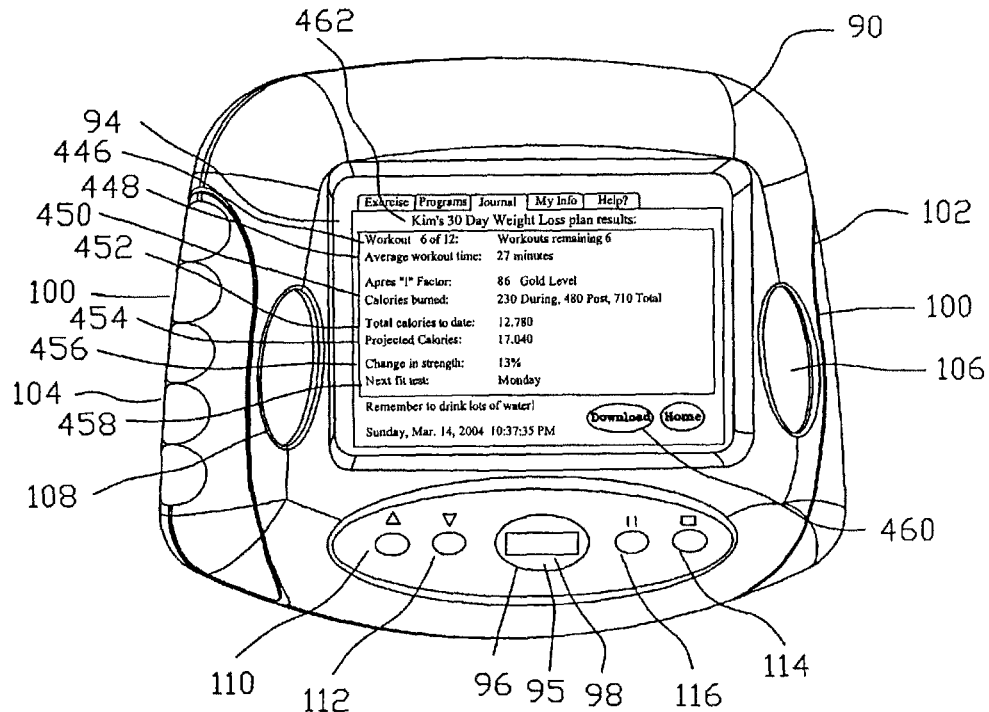
FIG. 40 is an enlarged view similar to FIG. 9.

FIG. 40 is a similar view of FIG. 39 displaying a second journal menu 462. The second journal menu 462 comprises an exercising schedule including a 30 day weight loss plan for the operator 12.

Figure 41:
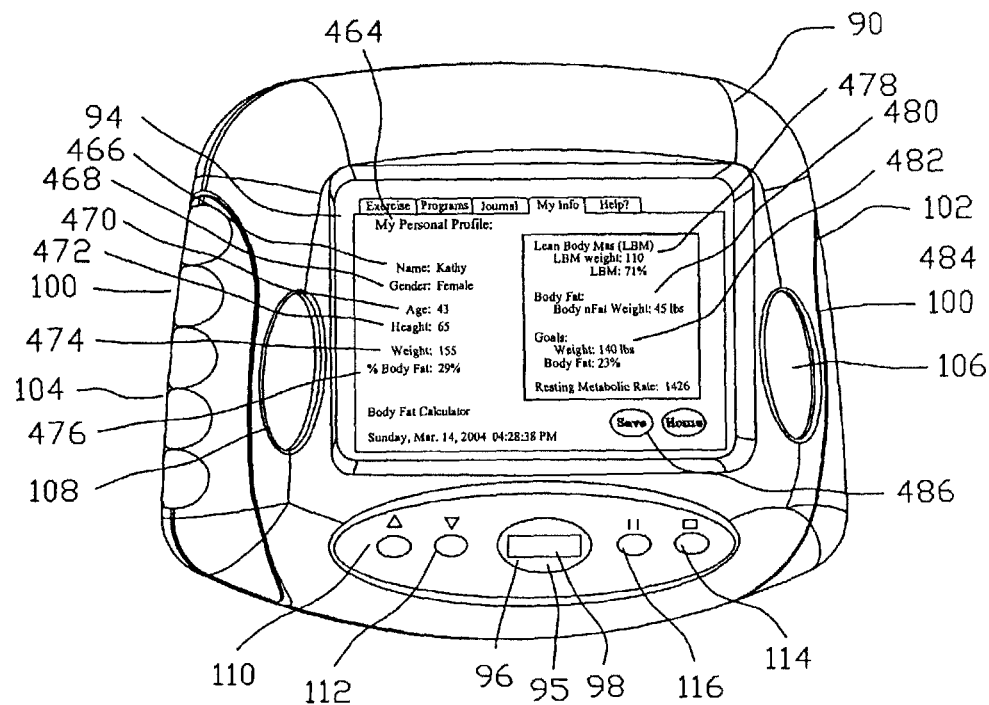
FIG. 41 is an enlarged view similar to FIG. 9.
Figure 42:
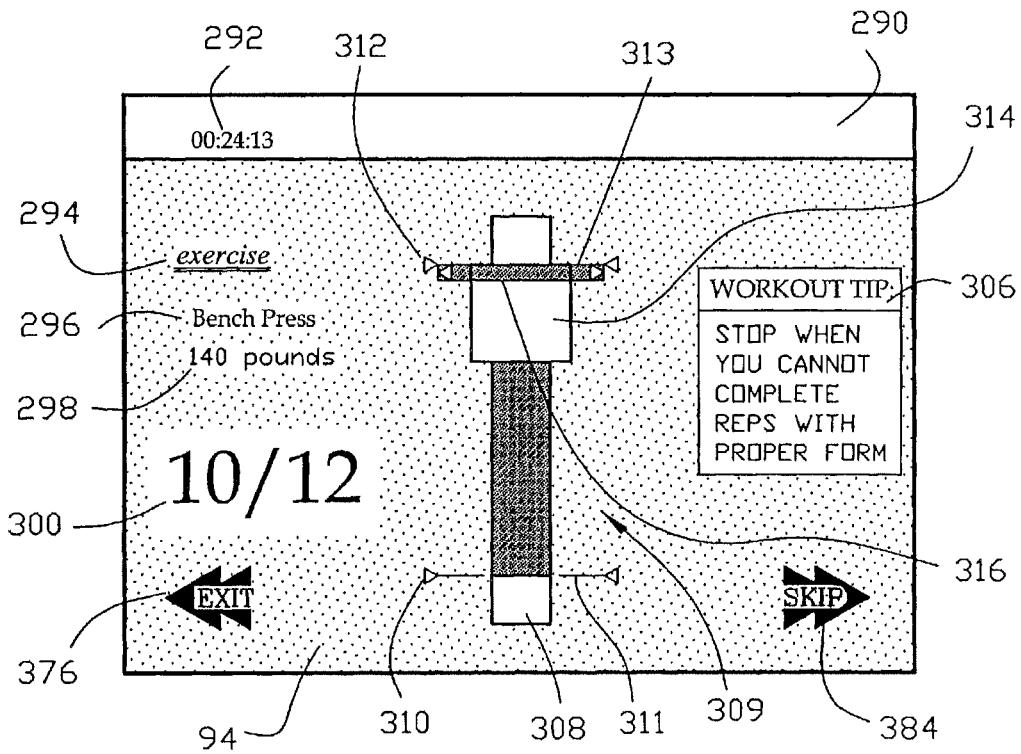
FIG. 42 is a view similar to FIG. 21 illustrating a moving scale and a moving bar in a maximum range of movement.
Figure 43:
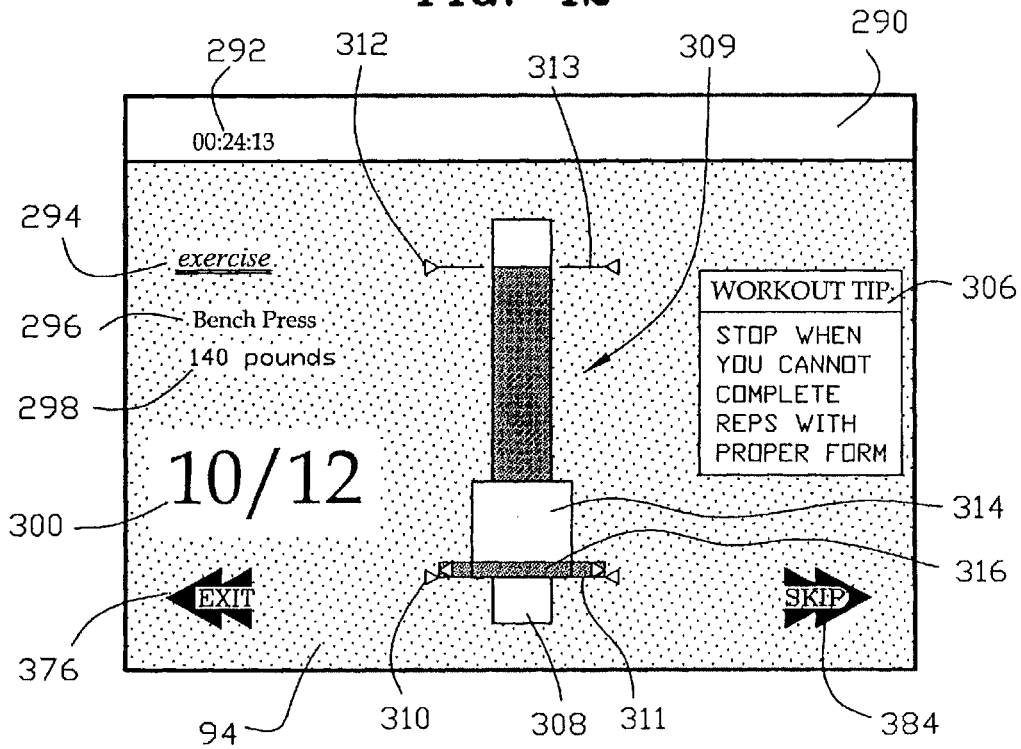
FIG. 43 is a view similar to FIG. 42 illustrating a moving scale and a moving bar in a minimum range of movement.

FIG. 41 illustrates the liquid crystal touch screen display 94 displaying a personal information menu 464. The personal information menu 464 comprises the operator's personal profile including name 466, gender 468, age 470, height 472, weight 474, percent body fat 476, lean body mass 478, body fat 480, goals 482 and resting metabolic rate 484. The personal information menu 464 may also include a save function 486 to save the operator's profile to the removable memory device 98.

As best seen in FIGS. 1-43, the subject invention further includes a process of enabling the operator 12 to exercise with the exercise device 10. Before the operator 12 utilizes the exercise device 10 to exercise, the operator 12 is preferably required to enter data into a computer for designing an individual exercising program. The data may be entered by utilizing the user interface 90, the rotary optical encoder 132 and the scale 170. Alternatively, the data may be entered by utilizing an alternative computer that will be described in more detail below.

The step of measuring a weight 474 of the operator may occur. The operator is positioned on the seat 24 to utilize the scale 170. The scale 170 forwards weight data to the application software for generating an electronic weight data. The exercising program may be designed based in part on the electronic weight data.

The step of measuring the resting and/or elevated heart rate 390 of the operator may occur. The operator positions his palms of this hands on the first and second contact pad 102 and 104 to utilize the heart rate contact 100. The heart rate contact 100 forwards heart rate data to the application software for generating a heart rate data. The exercising program may be designed based in part on the heart rate data.

The step of measuring the body fat index 476 of the operator may occur. The operator positions his palms of this hands on the first and second contact pad 102 and 104 to utilize the body fat index contact 100. The body fat index contact 100 forwards body fat index data to the application software for generating a body fat index data. The exercising program may be designed based in part on the body fat index data.

The step of inputting the numerical value for the age 470 of the operator may occur. The operator may utilize the liquid crystal touch screen display 94 of the user interface 90 to enter a numeric value. The user interface 90 forwards the numeric value to the application software for generating an electronic age data. The exercising program may be designed based in part on the electronic age data.

The step of inputting the numerical value for the height 472 of the operator may occur. The operator may utilize the liquid crystal touch screen display 94 of the user interface 90 to enter a numeric value. The user interface 90 forwards the numeric value to the application software for generating an electronic height data. The exercising program may be designed based in part on the electronic height data. Additional personal information such as gender 468, percent body fat 476, lean body mass 478, goals 482 and resting metabolic rate 484 may be inputted by a numerical value and utilized for designing an electronic program.

As best seen in FIGS. 11-14, 21, 22, 32, 42 and 43 a further step including determining the range of movement 309 of the press 50. The range of movement 309 is measured during the operator performing an exercise on the exercise device 10 by the rotary optical encoder 132. The rotary optical encoder 132 forwards a range data to the application software for generating an electronic range of movement data. The exercising program may be designed based in part on the electronic range of movement data. The electronic range of movement data is displayed on the liquid crystal touch screen display 94 as a lower range 310 and an upper range 312. The lower range 310 is designed by the electronic program to assign a minimum range of movement 311 of the press 50 for instructing the operator to terminate a negative loading motion of the press 50 during exercising. This minimum range of movement 311 is assigned preferably such that the operator does not remove the load developed within the muscles of the operator by positioning the load 38 in a resting position. The upper range 312 is designed by the electronic program to assign a maximum range of movement 313 of the press 50 for instructing the operator to terminate a positive loading motion of the press 50 before a joint of the operator enters into a locked position.

The rotary optical encoder 132 further forwards a distance and time data to the application software for generating an electronic rate of displacement data. The exercising program may be designed based in part on the electronic rate of displacement data. The rate of displacement data is displayed on the liquid crystal touch screen display 94 as an operator pace bar 316. The speed of the operator pace bar 316 is controlled by the rotary optical encoder 132 based on the movement of press 50. The program pace bar 314 is designed by the electronic program to provide the operator with a smooth speed and direction through both the positive and negative loading motions. Upon displacement of the press 50, the program pace bar 314 provides an ideal speed and direction for the press 50 as given by the display. The operator is instructed to displace the press 50 such the operator pace bar 316 remains within the program pace bar 314.

A further step includes measuring the strength of the operator during operation of the exercise device. Preferable, the exercising program instructs the operator to insert the pin 48 in a particular weight cavity 46 of the plurality of weights 40 for lifting a specified load 38. The rotary optical encoder 132 allows the exercising program to monitor the number of correctly performed positive and negative loading motions. The exercising program generates an electronic strength data in response to the number of correctly performed positive and negative loading motions. The exercising program may be designed based in part on the electronic strength data.

Once the measurements of the range of movement, strength, weight, and inputting age and height of the operator, the processor will design an electronic program to provide the operator with instructions for effectively utilizing the exercise device 10. The instructions may include the type of exercises to engage in, the number exercises to engage in, the number of positive and negative loading motions, the load amount to be displaced, the range of movement 309, the speed of program pace bar 314 and the time between exercising sets.

As best seen in FIGS. 21, 22, 24-43 the electronic program may program and illustrate a number of parameters during the operator utilizing the exercising device 10. For example, the electronic program may monitor and illustrate on the user interface module 90 the range of movement, strength, weight, heart rate, body fat index, the type of exercises conducted, the number exercises conducted, the number of positive and negative loading motions, the load value to be displaced, the range of movement 309, the speed of the operator pace bar 316, the ability to maintain the operator pace bar 316 within the program pace bar 314 and the time between exercising sets. As best seen in FIGS. 35, 39-41 the processor may generate and display performance data based on the range of movement, strength, weight, heart rate, body fat index, the type of exercises conducted, the number exercises conducted, the number of positive and negative loading motions, the load value to be displaced, the range of movement 309, the speed of the operator pace bar 316, the ability to maintain the operator pace bar 316 within the program pace bar 314 and the time between exercising sets.

As best seen in FIGS. 44-49 the processor preferably causes both the operator's customized electronic program and performance data to be stored in an electronic media 96. The electronic media may include a portable electronic storage device 98 linked to the processor through an electronic wire link 99. Alternatively, the electronic media may include a network electronic storage device 120 linked to the processor through an electronic wireless link 122.

The process may further include displaying an advertisement 1147 on said screen for marketing goods and services. The advertisement 1147 may include promotional material, advertising and/or entertainment material. Preferably, the advertisement 1147 is predominantly utilized between exercising sets.

Figure 44:
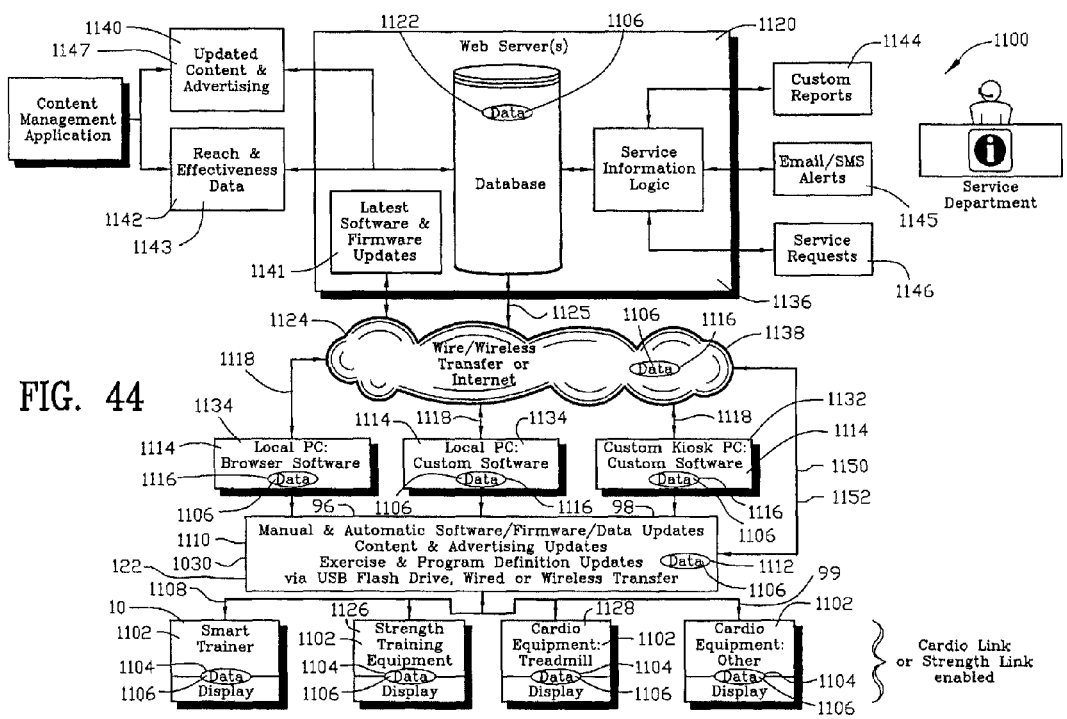
FIG. 44 is a block diagram illustrating an electrical network incorporating a second embodiment of the subject invention.

FIG. 44 illustrates another embodiment of the subject invention including an electrical network 1100 for enables an operator to exercise. The electrical network 1100 includes a plurality of exercise machines 1102 for enabling the operator to exercise. Each of said plurality of exercise machines 1102 have an exercise electric storage 1104 for storing data 1106 relative to the exercise of the operator on the plurality of exercise machines 1102 respectively. A serial link 1108 electrically couples the plurality of exercise machines 1102 for transferring the data 1106 relative to the exercise of the operator between the plurality of exercise machines 1102 respectively. A data transfer device 1110 has a transfer electric storage 1112 and is electrically coupled to the serial link 1108 for transmitting and receiving the data 1106 between the plurality of exercise machines 1102 and the data transfer device 1110. A local computer 1114 has a local electric storage 1116 for storing the data 1106 relative to the exercise of the operator on the plurality of exercise machines 1102 respectively. A local link 1118 electrically couples the data transfer device 1110 to the local computer 1114 for transmitting and receiving the data 1106 between the data transfer device 1110 and the local computer 1114. A remote computer 1120 has a remote electric storage 1122 for storing the data 1106 relative to the exercise of the operator on the plurality of exercise machines 1102 respectively. A wire, wireless or internet 1124 having a network link 1125 electrically couples the local computer 1114 to the remote computer 1120 for transmitting and receiving the data 1106 between the local computer 1114 and the remote computer 1120.

The plurality of exercise machines 1102 may include a strength training exercise 1126, a cardiovascular training exercise 1128 or other exercise devices. The data transfer device 1110 includes a removable solid state memory device 1130. The local computer 1114 may include an electronic kiosk 1132, personal computer 1134 or other computer devices. The remote computer 1120 may include a web server 1136. The wire, wireless or internet 1124 may include a world wide web 1138. The data may comprise an updated software 1140, updated firmware 1141, exercise performance 1142, exercise history 1143, custom reports 1144, alerts 1145, service requests 1146 and/or advertisements 1147.

Alternatively, the electrical network 1100 may include a wireless local link 1150 electrically coupling the data transfer device 1110 to the wire, wireless or internet 1124 for transmitting and receiving the data 1106 between the data transfer device 1110 and the remote computer 1120. The wireless local link 1150 may include a wireless local area network 1152 such as a Wi-Fi or other wireless local area network.

Figure 45:
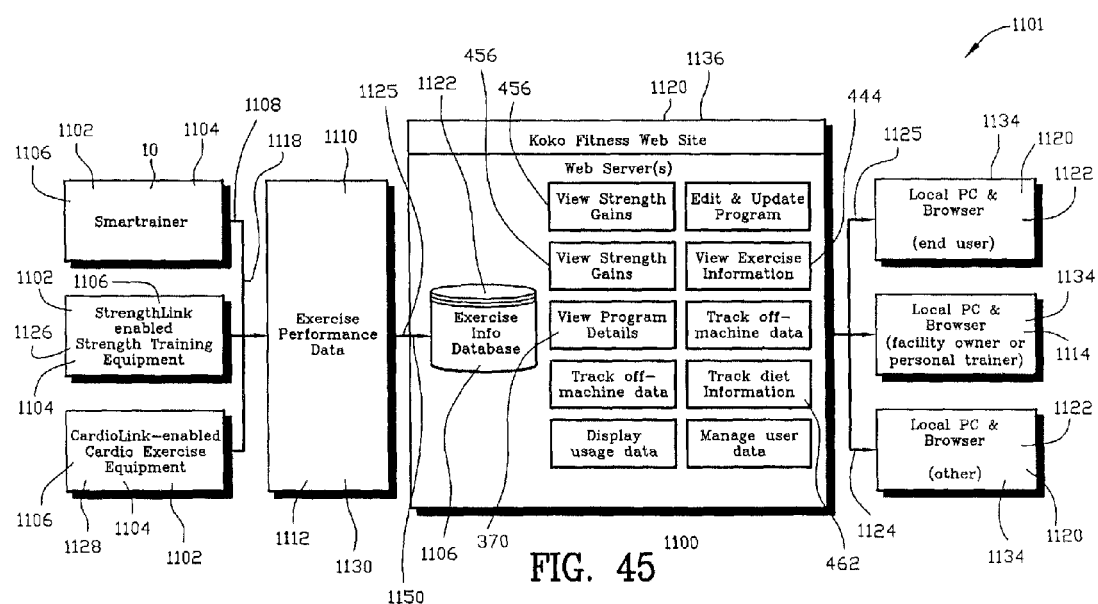
FIG. 45 is a block diagram illustrating an electrical network incorporating a third embodiment of the subject invention.

As best seen in FIGS. 44 & 45 illustrates another embodiment of the subject invention including an electrical network 1101 for enables an operator to exercise. The electrical network 1100 includes a plurality of exercise machines 1102 for enabling the operator to exercise. Each of said plurality of exercise machines 1102 have an exercise electric storage 1104 for storing data 1106 relative to the exercise of the operator on the plurality of exercise machines 1102 respectively. A serial link 1108 electrically couples the plurality of exercise machines 1102 for transferring the data 1106 relative to the exercise of the operator between the plurality of exercise machines 1102 respectively. A data transfer device 1110 has a transfer electric storage 1112 and is electrically coupled to the serial link 1108 for transmitting and receiving the data 1106 between the plurality of exercise machines 1102 and the data transfer device 1110. A remote computer 1120 has a remote electric storage 1122 for storing the data 1106 relative to the exercise of the operator on the plurality of exercise machines 1102 respectively. A network 1124 having a network link 1125 electrically couples the remote computer 1120 to the remote computer 1120. The remote computer 1120 may also be networked to a local computer 1114 to the remote computer 1120 for transmitting and receiving the data 1106 between the local computer 1114 and the remote computer 1120.

The plurality of exercise machines 1102 may include a strength training exercise 1126, a cardiovascular training exercise 1128 or other exercise devices. The data transfer device 1110 includes a removable solid state memory device 1130. The local computer 1114 may include an electronic kiosk 1132, personal computer 1134 or other computer devices. The remote computer 1120 may include a web server 1136. The network 1124 may include a world wide web 1138. The data may comprise an updated software 1140, updated firmware 1141, exercise performance 1142, exercise history 1143, custom reports 1144, alerts 1145, service requests 1146 and/or advertisements 1147.

Alternatively, the electrical network 1100 may include a wireless local link 1150 electrically coupling the data transfer device 1110 to the remote computer 1120 for transmitting and receiving the data 1106 between the data transfer device 1110 and the remote computer 1120. The wireless local link 1150 may include a wireless local area network 1152 such as a Wi-Fi or other wireless local area network.

Figure 46:
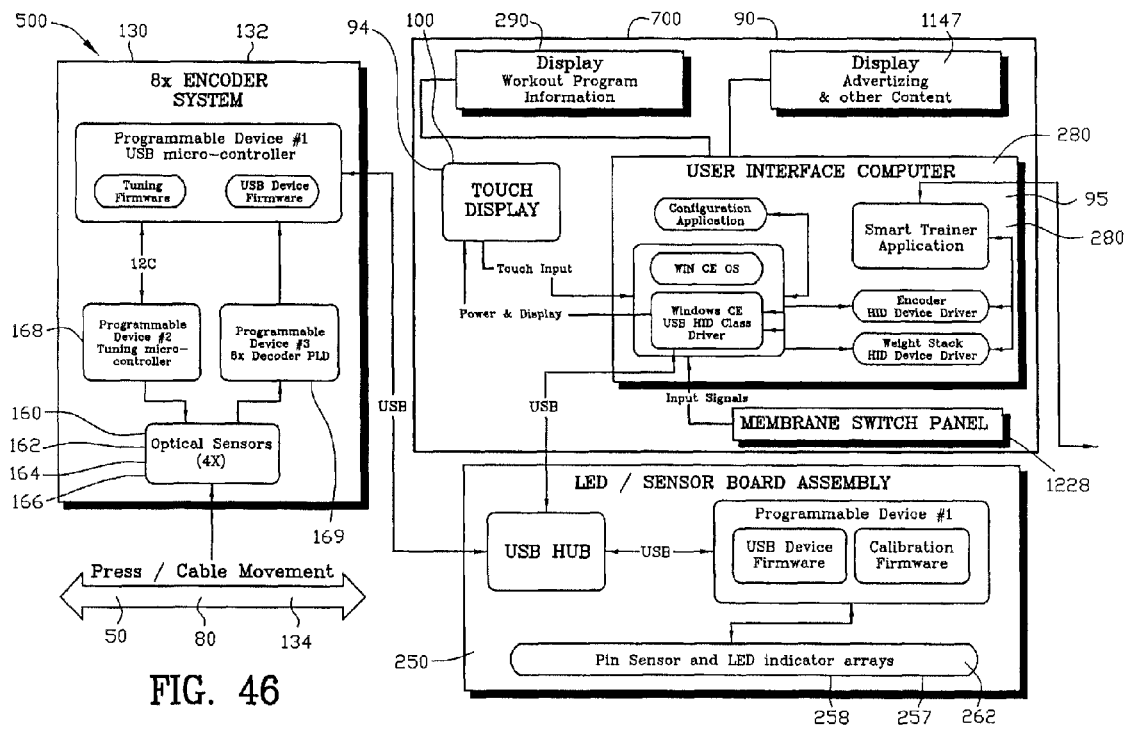
FIG. 46 is a first portion of a block diagram illustrating an electrical network incorporating a fourth embodiment of the subject invention.
Figure 47:
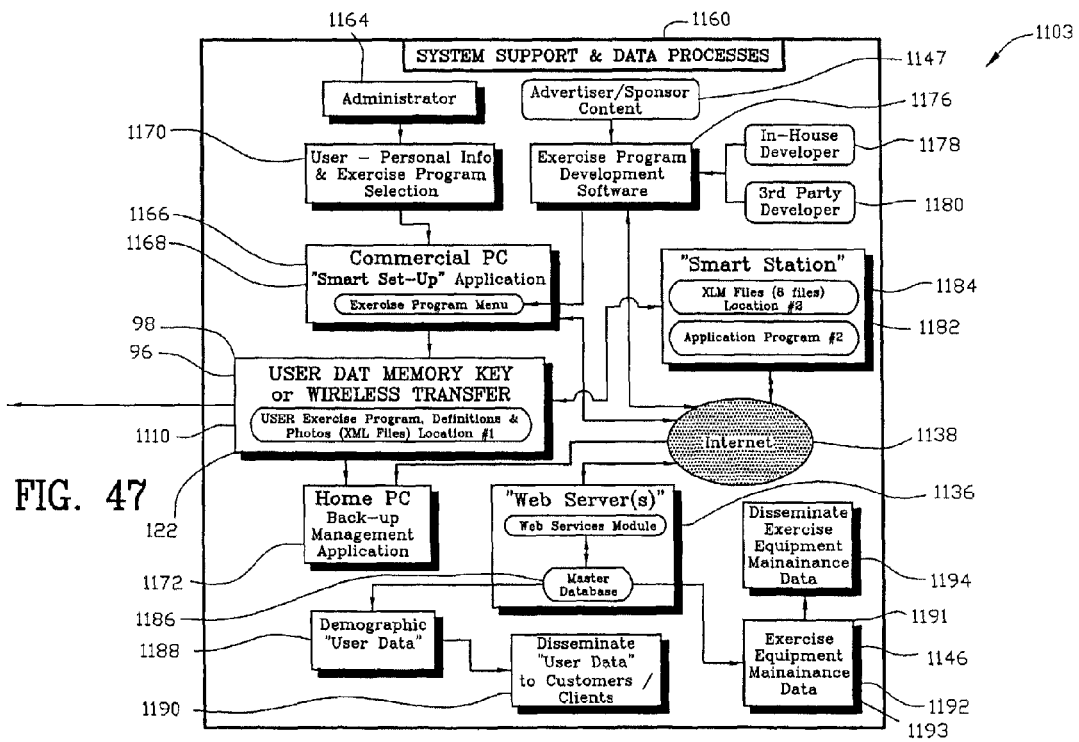
FIG. 47 is a second portion of a block diagram of FIG. 46.
Figure 48:
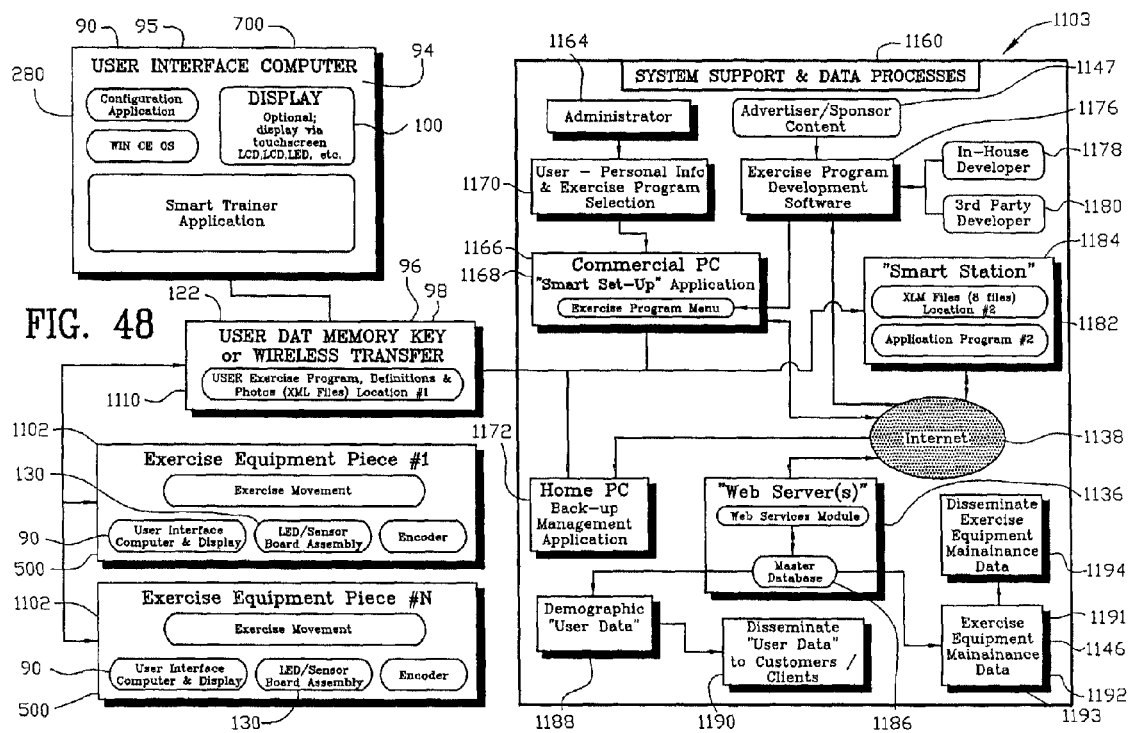
FIG. 48 is a block diagram illustrating an electrical network incorporating a fifth embodiment of the subject invention.

FIGS. 46-48 illustrates another embodiment of the subject invention including an electrical network 1103 for enables an operator to exercise. The electrical network 1103 includes an exercise apparatus 500 for enabling the operator to exercise. The exercise apparatus 500 includes an user interface 700, rotary optical encoder 132, weight encoder 250. The electrical network 1103 includes a system support & data processes network 1160. The system support & data processes network 1160 includes an administrator station 1164 serving a front desk of a gym. The administration station 1164 includes a local computer 1166 having a set-up program 1168 for inputting the operator's personal information and exercise program selection 1170. The operator's personal information may include their name, date of birth, gender, weight, height and operator's e-mail address. Operator selects a type of exercise program from a menu of exercise programs. Exercise program is further modified base on the strength test executed during the exercise program. The operator's personal information and exercise program selection 1170 is transferred to the data transfer device 1110. The data transfer device 1110 may be utilized with the operator's home personal computer 1172 to backup the operator's personal information and exercise program selection 1170.

Between exercising sets, the operator is instructed to rest for a time period. During this time period an advertiser/sponsor content material and/or exercising tips 1147 may be displayed on the user interface module 90. An exercise program development software 1176 may be created by either an in-house developer 1178 and/or a third party developer 1180 would wishes to create a novel exercise program. This exercise program development software 1176 is transferred to the local computer 1166 where the exercise program development software 1176 is then transferred to the data transfer device 1110 during the transferring of the operator's personal information and exercise program selection 1170.

After the operator has completed an exercise routine, the operator inserts the data transfer device 1110 into a local computer 1182. The local computer 1182 may include a kiosk 1184. The exercise performance data 1142 is then copied from the transfer device 1110 to the kiosk 1184. The kiosk 1184 includes an application program that processes the exercise performance data 1142 and exports the exercise performance data 1142 over the internet 1138 to the web server 1136. The web server 1136 includes a master database 1186 that houses all exercise performance data 1142. From the master database 1186 the exercise performance data 1142 may be extracted to a demographic data database 1188. The demographic data database 1188 may include data selected from a criteria including the operator's personal information and/or exercise performance data 1186. A data dissemination 1190 may then occur that transfers the data 1188 to any individual, group and/or government organization.

The insertion of the data transfer device 1110 into the exercising apparatus 500 transfers a duty cycle data 1191 and an error code data 1192 from the exercising apparatus 500 to the data transfer device 1110. The duty cycle data 1191 includes a record of the exercising apparatus 500 usage including the exercising apparatus 500 by serial number, location, installation date and the amount of load lifted by the apparatus 500. The error code data 1192 includes any malfunction of the exercising apparatus 500. Upon insertion of the data transfer device 1110 into the kiosk 1184, the duty cycle data 1191 and the error code data 1192 are transferred through the internet 1138 to the web server 1136. The duty cycle data 1191 and the error code data 1192 are complied into a duty/error code database 1193. The duty cycle data 1191 and the diagnostic code data 1192 may then be disseminated to a repair or service department 1194 to schedule the repair or service needed. A membrane switch 1228 comprises a plurality of switches positioned on the user interface 700. The membrane switch 1228 may be used to immediately stop or pause the exercising program. The membrane switch 1228 may also adjust the volume of speakers within the user interface 700. In addition, a depression of two or more of the plurality of switches in combination may place the exercise apparatus 500 into a testing or diagnostic mode. FIG. 48 illustrates another embodiment of the subject invention including an electrical network 1103 for enables an operator to exercise. FIG. 48 includes a plurality of exercise machines 1102 being utilized with the identical data transfer device 1110.

Figure 49:
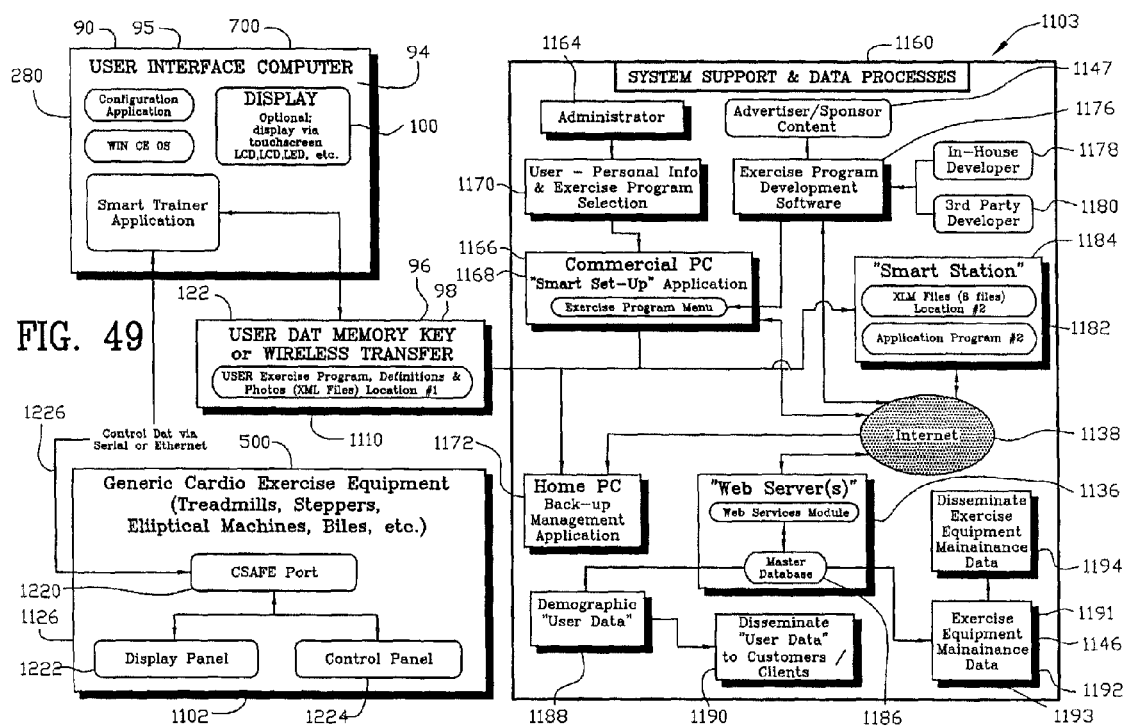
FIG. 49 is a block diagram illustrating an electrical network incorporating a sixth embodiment of the subject invention.

FIG. 49 illustrates another embodiment of the subject invention including an electrical network 1103 for enabling an operator to exercise. The exercise apparatus 500 utilizes an industry standard communication protocol that electrically couples a plurality of generic exercise machines to the user interface 700. The industry standard communication protocol establishes an industry wide communication specification for exercise devices. An industry standard communication protocol data is transferred from the generic exercise machine to the user interface 700 by either a serial or Ethernet cable. The user interface 700 includes a program to interpret the industry standard communication protocol format into the user interface format. By utilizing the industry standard communication protocol format in conjunction with the exercise apparatus 500 it is possible to utilize the data transfer device 1110 with any generic exercise machine that includes an industry standard communication protocol communication specifications.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A system, comprising:
   an exercise device, comprising:
      a first sensor coupled to the exercise device for measuring a range of movement of the operator during exercise on the exercise device;
      a second sensor coupled to the exercise device for measuring a strength of the operator during exercise on the exercise device;
      a processor electrically coupled to the first sensor and the second sensor to generate electronic range of movement data based on the range of movement of the operator measured by the first sensor and electronic strength data based on the strength of the operator measured by the second sensor; and
   a network;
   a remote computer configured to:
      receive over the network the electronic range of movement data and electronic strength data;
      produce an program of exercise instructions based on the electronic range of movement data and the electronic strength data; and
      store the program of exercise instructions in an electronic storage media.

2. The system of claim 1, wherein the exercise device is a first exercise device, and the system further comprises: a plurality of exercise devices including the first exercise device, with the plurality of exercise devices coupled by the network to the remote computer, and with each exercise device comprising:
   a display to render the program of exercise instructions.

3. The system of claim 1, further comprising:
   a scale for measuring a weight of the operator for generating electronic weight data to configure the remote computer to produce the program of exercise instructions based on the electronic weight data;
   a contact for measuring a heart rate of the operator when the operator touches the contact to generate an electronic heart rate data to configure the remote computer to produce the program of exercise instructions based on the heart rate data; and
   a body fat contact for measuring a body fat index of the operator during contacting the exercise device for generating a fat index data, to configure the remote computer to produce the program of exercise instructions based on based on the fat index data.

4. The system of claim 1, further comprising:
   a user interface for inputting numerical values into the exercise device for use with the remote computer to produce the program of exercise instructions.

5. The system of claim 1, further comprising the processor configured to:
   render on a display associated with the exercise device an operator pace bar for indicating a rate of displacement of exercise of the operator on the exercising device.

6. The system of claim 2 wherein the display renders exercise program performance as a moving scale on at least one display of at least one exercise device.

7. The system of claim 6, wherein the processor is configured to generate performance data based upon the effectiveness of the operator in maintaining an exercise rate similar to a rate of the moving scale.

8. The system of claim 7, further comprising the processor configured to:
   render on the display an operator pace bar to render the performance data on the exercising device relative to the moving scale.

9. The system of claim 7, further comprising: an electronic storage media for storing the performance data generated by the processor.

10. The system of claim 7, further comprising a port on the exercise device configured to accept a portable electronic storage device to store the performance data.

11. The system of claim 7, further comprising a network electronic storage device coupled to at least some of the exercise devices for storing performance data according to the operator of the some exercise devices.

12. The system of claim 1, further comprising the processor configured to render on a display an operator pace bar for indicating the rate of displacement of a positive loading motion and a negative loading motion of the operator on the exercising device based on the electronic program of exercise instructions.

13. The system of claim 2, further comprising the processor configured to render on a display an indicator of a maximum range of movement for instructing the operator to terminate a positive loading motion based on the electronic program of exercise instructions.

14. The system of claim 2, further comprising the processor configured to render on a display an indicator of a minimum range of movement for instructing the operator to terminate a negative loading motion based on the electronic program of exercise instructions.

15. The system of claim 2, further comprising the processor configured to render on the display of at least one of the plurality of exercise devices an advertisement for marketing goods and/or services.

16. A system, comprising:
   a plurality of exercise devices, at least some of the exercise devices comprising:
      a first sensor coupled to the exercise device for measuring a range of movement of the operator during exercise on the exercise device;
      a second sensor coupled to the exercise device for measuring a strength of the operator during exercise on the exercise device;
      a processor electrically coupled to the first sensor and the second sensor to:
         generate electronic range of movement data based on the range of movement of the operator measured by the first sensor and electronic strength data based on the strength of the operator measured by the second sensor; and
         generate an operator pace bar for indicating a rate of displacement of exercise of the operator on the exercising device;
      a display to render the pace bar; and a network interconnecting at least the some of the plural of exercise devices;

electronic storage media for storing the performance data generated by the processor;

a remote computer configured to:

receive over the network the electronic range of movement data and electronic strength data for each of the exercise devices;

produce corresponding programs of exercise instructions based on the electronic range of movement data and the electronic strength data received from each corresponding one of the at least some exercise devices; and store the corresponding program of exercise instructions in electronic storage media associated with the corresponding ones of the at least some of the exercise devices.

17. The system of claim 16, further comprising:

a scale for measuring a weight of the operator for generating electronic weight data to configure the remote computer to produce the program of exercise instructions based on the electronic weight data;

a contact for measuring a heart rate of the operator when the operator touches the contact to generate an electronic heart rate data to configure the remote computer to produce the program of exercise instructions based on the heart rate data; and a body fat contact for measuring a body fat index of the operator during contacting the exercise device for generating a fat index data, to configure the remote computer to produce the program of exercise instructions based on based on the fat index data.

18. The system of claim 16, further comprising:

a user interface for inputting numerical values into the exercise device for use with the remote computer to produce the program of exercise instructions.

19. The system of claim 16 wherein the display for each of the at least some exercise devices renders exercise program performance as a moving scale.

20. The system of claim 19, wherein the processor is configured to generate based on the program of exercise instructions the pace bar based upon the effectiveness of the operator in maintaining an exercise rate similar to a rate of the moving scale.

21. The system of claim 16, further comprising:

a port on the at least some exercise devices, the port configured to accept the electronic storage device to store the performance data.

22. The system of claim 16, further comprising:

network electronic storage device for storing performance data of operators of the at least some exercise devices.

23. The system of claim 16, further comprising the processor configured to:

render on the display the operator pace bar for indicating the rate of displacement of a positive loading motion and a negative loading motion of the operator on the exercising device based on the electronic program of exercise instructions.

24. The system of claim 23, further comprising the processor further configured to render on a display an indicator of a maximum range of movement for instructing the operator to terminate a positive loading motion based on the electronic program of exercise instructions and a minimum range of movement for instructing the operator to terminate a negative loading motion based on the electronic program of exercise instructions.

* * * * *